(12) United States Patent
Witchey et al.

(10) Patent No.: US 12,332,986 B2
(45) Date of Patent: Jun. 17, 2025

(54) CONTENT AUTHENTICATION AND VALIDATION VIA MULTI-FACTOR DIGITAL TOKENS, SYSTEMS, AND METHODS

(71) Applicants: Nant Holdings IP, LLC, Culver City, CA (US); ImmunityBio, Inc., Culver City, CA (US)

(72) Inventors: Luna Witchey, Laguna Hills, CA (US); John Zachary Sanborn, Santa Cruz, CA (US); Patrick Soon-Shiong, Los Angeles, CA (US); Nicholas James Witchey, Laguna Hills, CA (US)

(73) Assignees: Nant Holdings IP, LLC, Culver City, CA (US); ImmunityBio, Inc., Culver City, CA (US)

( * ) Notice: Subject to any disclaimer, the term of this patent is extended or adjusted under 35 U.S.C. 154(b) by 0 days.

(21) Appl. No.: 18/396,086

(22) Filed: Dec. 26, 2023

(65) Prior Publication Data
US 2024/0126856 A1    Apr. 18, 2024

Related U.S. Application Data

(63) Continuation of application No. 17/890,482, filed on Aug. 18, 2022, now Pat. No. 11,899,768, which is a
(Continued)

(51) Int. Cl.
*G06F 21/32*    (2013.01)
*G06F 21/60*    (2013.01)
(Continued)

(52) U.S. Cl.
CPC ............ *G06F 21/32* (2013.01); *G06F 21/602* (2013.01); *G06F 21/645* (2013.01); *G16B 50/40* (2019.02)

(58) Field of Classification Search
CPC ........ G06F 21/32; G06F 21/602; G06F 21/64; G06F 21/645; G16B 50/40
See application file for complete search history.

(56) References Cited

U.S. PATENT DOCUMENTS

| 5,708,825 | A  | * | 1/1998 | Sotomayor | ............. | G06F 40/30 |
| | | | | | | 707/E17.094 |
| 7,330,563 | B2 | * | 2/2008 | Rhoads | .............. | H04N 1/32203 |
| | | | | | | 704/E19.009 |

(Continued)

OTHER PUBLICATIONS

NPL Search Terms (Year: 2024).*
(Continued)

*Primary Examiner* — Syed A Zaidi
(74) *Attorney, Agent, or Firm* — Sheridan Ross P.C.

(57) ABSTRACT

Authentication tokens, systems, and methods are described. An illustrative method is disclosed to include receiving an electronic file including a digital image, receiving biometric information that is associated with a person, modifying the electronic file with the biometric information such that one or more pixels in the digital image are replaced with the biometric information, and storing the modified electronic file as a digital authentication token to be used in connection with authorized publications of original digital work.

21 Claims, 21 Drawing Sheets

Related U.S. Application Data continuation of application No. 17/556,887, filed on Dec. 20, 2021, now Pat. No. 11,455,385, which is a continuation of application No. 17/360,066, filed on Jun. 28, 2021, now Pat. No. 11,210,383, which is a continuation of application No. 17/111,278, filed on Dec. 3, 2020, now Pat. No. 11,048,788, which is a continuation of application No. 16/891,364, filed on Jun. 3, 2020, now Pat. No. 10,885,173.

(60) Provisional application No. 63/031,038, filed on May 28, 2020, provisional application No. 62/856,917, filed on Jun. 4, 2019.

(51) Int. Cl.
*G06F 21/64* (2013.01)
*G16B 50/40* (2019.01)

(56) References Cited

U.S. PATENT DOCUMENTS

| | | | |
|---|---|---|---|
| 8,468,355 | B2 | 6/2013 | Gerdes, Jr. et al. |
| 8,621,240 | B1* | 12/2013 | Auchmoody ....... G06F 21/6272 713/193 |
| 9,836,759 | B2 | 12/2017 | Georgi |
| 10,050,959 | B2 | 8/2018 | Soon-Shiong et al. |
| 10,735,782 | B2 | 8/2020 | Gordon |
| 10,735,827 | B2 | 8/2020 | Ng et al. |
| 10,885,173 | B2 | 1/2021 | Witchey |
| 11,048,788 | B2 | 6/2021 | Witchey et al. |
| 11,210,383 | B2 | 12/2021 | Witchey et al. |
| 11,455,385 | B2 | 9/2022 | Witchey et al. |
| 2001/0055411 | A1 | 12/2001 | Black |
| 2002/0056043 | A1 | 5/2002 | Glass |
| 2002/0138438 | A1* | 9/2002 | Bardwell ............... G06V 40/10 705/51 |
| 2002/0196963 | A1* | 12/2002 | Bardwell ............... G06K 19/12 382/126 |
| 2004/0034783 | A1 | 2/2004 | Fedronic et al. |
| 2004/0131184 | A1 | 7/2004 | Wu et al. |
| 2004/0158731 | A1 | 8/2004 | Narin et al. |
| 2005/0111466 | A1 | 5/2005 | Kappes et al. |
| 2006/0272031 | A1* | 11/2006 | Ache .................. H04N 21/6581 348/E7.071 |
| 2006/0277274 | A1* | 12/2006 | Tosey .................. G06F 16/9566 707/E17.115 |
| 2007/0088957 | A1 | 4/2007 | Carson |
| 2007/0136198 | A1 | 6/2007 | Foth et al. |
| 2007/0194751 | A1 | 8/2007 | Odaohhara |
| 2009/0165128 | A1 | 6/2009 | McNally et al. |
| 2009/0324061 | A1* | 12/2009 | Odgers ................... G06T 1/005 382/162 |
| 2011/0184791 | A1 | 7/2011 | Wang |
| 2012/0066508 | A1 | 3/2012 | Lentini |
| 2012/0317239 | A1 | 12/2012 | Mulder et al. |
| 2013/0226813 | A1 | 8/2013 | Voltz |
| 2013/0254533 | A1 | 9/2013 | Welch et al. |
| 2014/0101434 | A1 | 4/2014 | Senthurpandi et al. |
| 2014/0114675 | A1 | 4/2014 | Soon-Shiong |
| 2014/0123237 | A1 | 5/2014 | Gaudet et al. |
| 2014/0282965 | A1 | 9/2014 | Sambamurthy et al. |
| 2014/0289842 | A1 | 9/2014 | Cornick et al. |
| 2014/0368703 | A1* | 12/2014 | Yao ........................ H04N 25/75 348/295 |
| 2015/0149362 | A1 | 5/2015 | Baum et al. |
| 2015/0161370 | A1 | 6/2015 | North et al. |
| 2015/0309502 | A1 | 10/2015 | Breitgand |
| 2015/0326570 | A1 | 11/2015 | Publicover et al. |
| 2016/0012465 | A1 | 1/2016 | Sharp |
| 2017/0243193 | A1* | 8/2017 | Manian .............. G06Q 20/3829 |
| 2018/0082043 | A1 | 3/2018 | Witchey et al. |
| 2018/0096497 | A1* | 4/2018 | Bennett ..................... G06T 5/00 |
| 2018/0146370 | A1 | 5/2018 | Krishnaswamy et al. |
| 2018/0359811 | A1 | 12/2018 | Verzun et al. |
| 2019/0121989 | A1 | 4/2019 | Mousseau et al. |
| 2019/0149334 | A1 | 5/2019 | Van Der Velden |
| 2019/0171849 | A1 | 6/2019 | Assenmacher |
| 2019/0260721 | A1 | 8/2019 | O'Regan et al. |
| 2019/0327094 | A1* | 10/2019 | Kan ......................... H04L 9/50 |
| 2020/0007311 | A1 | 1/2020 | Oberhofer et al. |
| 2020/0127839 | A1 | 4/2020 | Alzahrani et al. |
| 2020/0366669 | A1* | 11/2020 | Gupta .............. G06K 19/06028 |
| 2021/0150003 | A1 | 5/2021 | Smaiely et al. |
| 2022/0405371 | A1 | 12/2022 | Witchey et al. |

OTHER PUBLICATIONS

NPL Search Terms (Year: 2025).*
Dong, Jinjin et al. Template Protection Based on DNA Coding For multimodal biometric recognition. 2017 4th International Conference on Systems and Informatics (ICSAI). https://ieeexplore.ieee.org/stamp/stamp.jsp?tp=&arnumber=8248565 (Year: 2017).
C.S., Sreeja; Misbahuddin, Mohammed. An Online Signature Method Using DNA based Bio-Hash for Positive Identification and Non-Repudiation. 2017 International Conference on Public Key Infrastructure and its Applications (PKIA). https://ieeexplore.ieee.org/stamp/stamp.jsp?tp=&arnumber=8278957 (Year: 2017).
Lee, Hyobin et al. Biometric Image Authentication using Watermarking. 2006 SICE-ICASE International Joint Conference. https://ieeexplore.ieee.org/stamp/stamp.jsp?tp=&arnumber=4108459 (Year: 2006).
Peethala, Manjari Benhar; Kulkarni, Sujata. Integrating Biometric Cryptosystem with steganography for authentication. 2016 IEEE International WIE Conference on Electrical and Computer Engineering (WIECON-ECE). https://ieeexplore.ieee.org/stamp/stamp.jsp?tp=&arnumber=8009080 (Year: 2016).
Motwani, Rakhi C., Frederick C. Harris Jr, and Kostas E. Bekris. "A proposed digital rights management system for 3d graphics using biometric watermarks." 2010 7th IEEE Consumer Communications and Networking Conference. IEEE, 2010. (Year: 2010).
Milano, Dominic. "Content control: Digital watermarking and fingerprinting." White Paper, Rhozet, a business unit of Harmonic Inc., http://www.rhozet.com/whitepapers/Fingerprinting-Watermarking.pdf, Last accessed May 30, 2012. (Year: 2012).
Kakar, Pravin, Natarajan Sudha, and Wee Ser. "Exposing digital image forgeries by detecting discrepancies in motion blur." IEEE Transactions on Multimedia 13.3 (2011): 443-452. (Year: 2011).
NPL Search Terms (Year: 2021).
NPL Search Terms (Year:.
NPL Search Terms (Year: 2023).
Official Action for U.S. Appl. No. 16/891,364, dated Oct. 29, 2020 9 pages.
Notice of Allowance for U.S. Appl. No. 16/891,364, dated Nov. 16, 2020 9 pages.
Notice of Allowance for U.S. Appl. No. 17/111,278, dated Mar. 8, 2021 10 pages.
Notice of Allowance for U.S. Appl. No. 17/360,066, dated Aug. 13, 2021 11 pages.
Official Action for U.S. Appl. No. 17/556,887, dated Mar. 21, 2022 8 pages.
Notice of Allowance for U.S. Appl. No. 17/556,887, dated May 19, 2022 9 pages.
Official Action for U.S. Appl. No. 17/890,482, dated Oct. 25, 2022 19 pages.
Final Action for U.S. Appl. No. 17/890,482, dated Jan. 26, 2023 20 pages.
Advisory Action for U.S. Appl. No. 17/890,482, dated Apr. 4, 2023 5 pages.
Official Action for U.S. Appl. No. 17/890,482, dated Jun. 12, 2023 20 pages.
Notice of Allowance for U.S. Appl. No. 17/890,482, dated Sep. 27, 2023 9 pages.

* cited by examiner

CONTENT AUTHENTICATION AND VALIDATION VIA MULTI-FACTOR DIGITAL TOKENS, SYSTEMS, AND METHODS

CROSS REFERENCE TO RELATED APPLICATIONS

The present application is a continuation of U.S. patent application Ser. No. 17/890,482 filed Aug. 18, 2022, which is a continuation of U.S. patent application Ser. No. 17/556,887 filed Dec. 20, 2021, now U.S. Pat. No. 11,455,385 issued Sep. 27, 2022, which is a continuation of U.S. patent application Ser. No. 17/360,066 filed Jun. 28, 2021, now U.S. Pat. No. 11,210,383 issued Dec. 28, 2021, which is a continuation of U.S. patent application Ser. No. 17/111,278 filed Dec. 3, 2020, now U.S. Pat. No. 11,048,788 issued Jun. 29, 2021, which is a continuation of U.S. patent application Ser. No. 16/891,364 filed Jun. 3, 2020, now U.S. Pat. No. 10,885,173 issued Jan. 5, 2021, which claims the benefit of and priority to U.S. Provisional Application No. 63/031,038 filed May 28, 2020, and U.S. Provisional Application No. 62/856,917 filed Jun. 4, 2019, the entire disclosures of which are hereby incorporated by reference.

FIELD OF THE DISCLOSURE

Embodiments of the present disclosure relate to systems and methods for generating and using authentication tokens.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As news and information continues to be distributed via social media providers rather than through reputable news sources, the news and information can be easily altered without anyone being aware of the alteration. The unfortunate result is that misinformation spreads and people can easily fall prey to fake news or conspiracy theories.

SUMMARY

It is with respect to the above that embodiments of the present disclosure were contemplated. In particular, embodiments of the present disclosure aim to solve problems associated with the generation and distribution of fake news or altered news stories, among other things. In particular, there is a need for a system that provides greater authenticity of information as well as accountability for those producing/publishing information.

In some embodiments, for digital media, a technique that combines information about the author and the content into an immutable authentication token may prove quite useful. The authentication token, in some embodiments, would digitally represent or notarize that the author did indeed create or have access to the content at the point of release/publication. Any modification to the published content would likely result in an interruption or distortion of the authentication token, thereby enabling consumers of the published content to quickly and easily discern the original and authentic published content from unauthorized modified versions of the original content.

In some embodiments, a digital authentication token may be provided or generated representing that an author created a specific work or piece of digital media content, including at specific points in time.

The digital authentication token, in some embodiments, may combine multiple factors of authentication and validation into a single digital entity. Examples of factors that can be retrieved and used to produce the digital authentication token can include, without limitation: an author's biometric or intrinsic data (e.g., iris information, DNA sequence information, vital signs, portions of DNA sequence information, fingerprint, etc.), an image of the author (e.g., portrait, photograph, voice, etc.), the digital content itself, an external notarization token (e.g., a blockchain hash, a certification token, etc.), a timestamp, a location, or other factors.

The following describes a single, non-limiting, embodiment of a method that can be used to produce an authentication token for use in protecting or securing digital media content. However, numerous variations are possible.

The digital authentication token can be created by first obtaining a digital image or video of the author (e.g., GIF, TIFF, JPG, PNG, BMP, SVG, MP4, M4A, etc.). Thereafter, a biometric or multiple biometrics of the author may be obtained. As a non-limiting example, a DNA sequence that is specific to the author may be obtained. This DNA sequence could be identifying genomic sequences, one or multiple Single Nucleotide Polymorphisms (SNPs), mutations relative to reference point, a transcription profile, a known proteomic mutation, INDELs, rearrangements, etc. In some embodiments, the DNA information (or other sequence information) may be specific to the author (or a publisher, editor, person, animal, etc.) and should not change significantly over time. The sequence may include a sufficient number of base pairs for the process. As a specific, but non-limiting example, there can be as many base pairs in the sequences as there are modifiable elements of the digital content (e.g., pixels in a digital image, letters in an article, words in an article, etc.).

In some embodiments, a virtual sequence may be created from the DNA sequence described above using a secret deterministic function. This virtual sequence may be created to protect the privacy of the author, editor, publisher, entity, etc. and could be created with a secret private key that is known to the person from whom the DNA sequence was obtained.

The method may then continue by obtaining a digital representation of the work (e.g., an article, an image, a video, a 3D rendering, a game, an X-ray, text file, binary file, etc.). The digital representation of the work may be converted into an original digital work token using a SHA-256 hash value or other identifying technique (e.g., check sum, MD5 hash, scrypt, etc.), for example.

The original digital work token may then be combined with a deterministic random number generator (RNG) or other function to modify the virtual sequence into a work sequence. The work sequence, in some embodiments, may have all letters in the sequence changed or just a few as desired, for example, according to privacy requirements of the author.

If the digital representation of the work corresponds to an image, then each pixel (or a selected subset of pixels) in the image may be replaced with a letter from the work sequence or other feature, for example the pixel can be replaced with an A, T, C, or G from a DNA sequence. The letter may be assigned a corresponding font and font size, which may or may not depend upon the characteristics of the pixel being replaced with the letter. In some embodiments, the letter is given the same color as the pixel. If the font used for the letter is bigger than the pixel, the resulting image will be larger than the original. This may or may not be selected (e.g., a larger font), depending upon a desired size output of the authentication token. The resulting image is the final digital authentication token that can be combined, appended, or otherwise attached to an original digital work before publication.

When the original digital work is published, it can be published with the final form of the digital authentication token either physically printed thereon, attached thereto, incorporated therein, rendered with, or combinations thereof. The digital authentication token, in some embodiments, carries information about the author, the work, an image of the author, and other factors.

It should be appreciated that other considerations can be addressed. For instance, the original digital work can be modified before, after, or while the digital authentication token is appended thereto or combined therewith.

In some embodiments, an image can be updated based on the foreground relative to background (e.g., using background separation).

In some embodiments, a mask can be used to mask out portions of the image that should not be updated, changed, or otherwise modified with the digital authentication token.

In some embodiments, the size of the font can be determined by the corresponding publishing format. For example, a high-fidelity printer could print very small fonts. A digital version can be resized and may, therefore, be capable of utilizing different font sizes depending upon the publication channel.

In some embodiments, the colors can be updated to create a watermark in the image itself.

In some embodiments, the digital work can include text, images, video, audio, or other types of digital data.

In some embodiments, the work sequence could be determined via use of a rolling hash. As an example, a next hash could be set equal to the next letter with the current hash. The result indicates if the next letter should change or not.

In some embodiments, rather than using DNA, one could alter the nature of a person's face in an image, say their iris as part of generating the digital authentication token.

In some embodiments, for physical works, such as for paintings, the brush strokes can be used as part of a security key. It may be possible to simulate brush strokes in a deterministic fashion.

In some embodiments, the original digital work may correspond to a dynamically-changing set of data (e.g., an audio stream, video stream, vital signs, workflow stages, etc.). In such an embodiment, the original digital work may correspond to a byte stream and other factors, such as author voice prints, frequency characteristics, etc. could be used to generate the digital authentication token.

In some embodiments, the digital authentication token could be static (e.g., a still image) or dynamic (e.g., animated or movable), possibly with a synchronization to the original digital work (e.g., synchronized with video).

In some embodiments, the resulting publication event, along with the digital authentication token, could be memorialized on a distributed ledger (e.g., bitcoin, Ethereum, TRON, hashgraph, IOTA, Microsoft's blockchain workbench, Hyperledger, Openchain, etc.). In some embodiments, distributed ledger technologies that are built to store data or form smart contracts such as Ethereum may be preferable.

The combinatorics of this approach are quite extensive. For example, just from a DNA perspective (among many other biometrics), one could use introns, exons, WGS, SNPs, INDELs, rearrangements, transcription profiles, known proteomic mutations, tissue of origin, or many other flavors of DNA (or RNA) as part of generating a digital authentication token.

One aspect of the present disclosure is to create a style for presenting an author along with their work. Although the disclosed "style" focuses on DNA, the technology described herein and the claims presented below should not be construed as being limited to DNA sequence information as the sole information used in connection with generating a digital authentication token.

Another aspect of the present disclosure is to provide genotype pixels that represent a single genomic position. In some embodiments, each subpixel of a genotype pixel may represent a particular nucleotide (e.g., A, C, G, T). As a non-limiting example, a genotype pixel may include four subpixels. If a subpixel is a first color or has a first value (e.g., is white), then the corresponding nucleotide is present in the patient's genotype of that genomic position. As a non-limiting example, a genotype pixel having only one white subpixel may indicate a homozygous genotype. A genotype pixel having two white subpixels may represent a heterozygous genotype (order may or may not matter). A genotype pixel having three or more white subpixels may be forbidden and considered an error. The detection of such a genotype pixel within an image may be exploited for purposes of image processing and decoding.

Although examples will be described with reference to a genotype pixel, it should be appreciated embodiments of the present disclosure contemplate utilizing any collection of two or more pixels and such collections of two or more pixels may be referred to as a pixel group. The subpixels belonging to or making up a pixel group may be organized in an array (e.g., a 2×2 square), a row (e.g., a 4×1 row), a column (e.g., a 1×4 column), or the like. An image may be made entirely of pixel groups or may be a combination of pixels and pixel groups. An image may be made almost entirely of individual pixels, but a predetermined area (e.g., a center, corner, etc.) of the image may be dedicated to having a pixel group provided therein while the remainder of the image may be composed of individual pixels rather than a pixel group.

In embodiments utilizing a pixel group (e.g., a genotype pixel), there may be an opportunity to identify allowed genotype pixels (e.g., an allowable pixel group) as well as forbidden genotype pixels (e.g., a forbidden pixel group). Knowledge of allowed genotype pixels and forbidden genotype pixels can be used during image processing to determine if any individual pixels were improperly encoded or improperly decoded/read (e.g., because they belong to a forbidden genotype pixel). The identification of forbidden genotype pixels within an image can be used to determine read errors for the image and/or to quickly identify whether an image has been fraudulently generated. In some embodiments, the presence of forbidden genotype pixels (e.g., forbidden image states) may provide a direct measure of a read error rate. Image reading/decoding processes can be designed to minimize a number of forbidden image states or forbidden genotype pixels.

In some embodiments, image security may be enhanced via shuffling. For instance, different seeds for a deterministic RNG may be used to generate different shuffled pixel maps such that each pixel map generated with a different seed value may be unique while still based on a deterministic shuffling of the same reference pixel map. A seed used for these purposes may correspond to any numeric value. As a non-limiting example, a seed or seed value may be generated from a digital hash of a file and/or password. A reference pixel map may be stored in server memory and may be randomly shuffled prior to storage, thereby making it difficult or impossible for someone to reverse engineer a patient's genotype based on a viewing of an image encoded with the patient's genomic information.

Image and identity validation may be achieved with knowledge of a seed and by enabling a server to match a shuffled reference image generated based on the seed with another image provided to the server that was also generated with the same seed. In this way, only information about the seed value needs to be shared between a client and server and there is no requirement to expose a patient's genomic information directly within an image without some level of obfuscation.

In some embodiments, a computer implemented method for proving authenticity of digital content is provided that includes:
  obtaining, with a processor, biometric information for a creator of an original digital work;
  modifying, with the processor, a work token with the biometric information to create a work sequence;
  modifying, with the processor, an electronic file that contains information descriptive of the creator of the original digital work, where the electronic file is modified with the work token to create a binding relationship between the biometric information for the creator of the original digital content and the electronic file;
  storing the modified electronic file as a digital authentication token; and
  enabling the stored digital authentication token to be accessed and used in connection with a publication of the original digital work.

In some embodiments, the biometric information includes DNA sequence information for the creator of the original digital work and the electronic file includes an image of the creator of the original digital work.

In some embodiments, the method includes replacing at least one pixel from the image of the creator of the original digital work with at least one letter obtained from the DNA sequence information.

In some embodiments, the DNA sequence information includes at least one of introns, exons, WGS, SNPs, INDELs, rearrangements, transcription profiles, known proteomic mutations, and a tissue of origin.

In some embodiments, the method further includes modifying at least some of the DNA sequence information based on a deterministic function to produce a virtual sequence and using the virtual sequence to modify the electronic file.

In some embodiments, a plurality of pixels in the image of the creator are replaced with characters representing the DNA sequence information for the creator and a font, size, and color of the characters are selected based upon a size and color of the plurality of pixels.

In some embodiments, the method further includes determining a publication modality to be used in connection with the publication of the original digital work and customizing the digital authentication token based on the publication modality.

In some embodiments, determining the publication modality includes determining a media type and whether the digital authentication token is capable of being presented via the publication modality in a static or dynamic manner. The method may further include matching a presentation of the digital authentication token with the media type and selecting either a static or dynamic digital authentication token based on whether the publication modality is capable of presenting the digital authentication token in a static or dynamic manner.

In some embodiments, the electronic file includes at least one of an image of the author or the original digital work itself.

In some embodiments, the method further includes combining the digital authentication token with the original digital work to produce publishable content, where combining comprises at least one of attaching the digital authentication token to the original digital work, providing a link in the original digital work to the digital authentication token, updating the original digital work to include a presentation of the digital authentication token, and displaying the digital authentication token as part of displaying the original digital work, and enabling the publishable content to be retrieved by one or more client devices via a communication network.

In some embodiments, a computer implemented method is described to include:
  receiving, at a processor, an electronic file comprising a digital image;
  receiving, at the processor, biometric information that is associated with a person;
  modifying, with the processor, the electronic file with the biometric information such that one or more pixels in the digital image are replaced with the biometric information; and
  storing the modified electronic file as a digital authentication token to be used in connection with authorized publications of original digital work.

In some embodiments, the biometric information includes DNA sequence information for the person and the person corresponds to an author, publisher, producer, or editor of the original digital content.

In some embodiments, the digital image includes an image of the person.

In some embodiments, one or more characters from the DNA sequence information are used to replace the one or more pixels.

In some embodiments, the DNA sequence information includes a virtual sequence that is generated based on an actual DNA sequence of the person and then obfuscated with a deterministic function to create the virtual sequence and characters from the virtual sequence are used to replace the one or more pixels.

In some embodiments, all pixels in the digital image are replaced with a character from the DNA sequence information.

In some embodiments, the original digital content is published via a web-based publication modality.

In some embodiments, the digital authentication token is presented along with the authorized publication of the original digital work.

In some embodiments, the modified electronic file includes a modified digital image of the person.

In some embodiments, the modified electronic file includes at least one of a still image and dynamic images.

In some embodiments, the one or more pixels are organized into a genotype pixel. The genotype pixel may include a plurality of the one or more pixels. As a non-limiting example, the genotype pixel may include four pixels with each pixel representing a nucleotide (e.g., A, C, G, T) within a patient's genotype of a particular genomic position. In some embodiments, the genotype pixel may correspond to an allowed genotype pixel or a forbidden genotype pixel. A forbidden genotype pixel may include three or four positive indicators of a presence of a nucleotide (e.g., three or four of the one or more subpixels constituting the genotype pixel may indicate a presence of a corresponding nucleotide).

In some embodiments, if an image is being processed and is determined to have more than a predetermined number (or percentage) of forbidden genotype pixels, then further processing of the image may be paused and a new image may be requested. The existence of such forbidden genotype pixels may represent that a read error occurred during the capture of the image.

In some embodiments, an image processing method may include determining a number of forbidden genotype pixels in an image and suspending further processing of the image. The method may further include returning an error message to a client device that captured the image. By performing an analysis of image quality based on forbidden genotype pixels, embodiments of the present disclosure effectively minimize the unnecessary commitment of image processing resources until an image of appropriate quality is obtained.

In some embodiments, a genotype pixel may correspond to a 2×2 array of the one or more pixels. In some embodiments, the genotype pixel may correspond to a 1×4 or 4×1 array of the one or more pixels.

In some embodiments, a pixel map containing a plurality of genotype pixels may be generated based on a patient's genotype for a predetermined number of genomic positions. The method may further include obfuscating the patient's genotype information by applying a hash function to the pixel map, thereby resulting in a shuffled pixel map. Method for storing the shuffled pixel map rather than the pixel map containing potentially private patient information help to ensure patient privacy and information security. Multiple different shuffled pixel maps may be generated with different seed values and/or deterministic functions and each different shuffled pixel map may be used for different servers and/or different authentication tokens.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Various objects, features, aspects and advantages of the inventive subject matter will become more apparent from the following detailed description of preferred embodiments, along with the accompanying drawing figures in which like numerals represent like components.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity may refer to one or more of that entity. As such, the terms "a" (or "an"), "one or more" and "at least one" can be used interchangeably herein. It is also to be noted that the terms "comprising", "including", and "having" can be used interchangeably. Also, as used in the description herein, the meaning of "in" includes "in" and "on" unless the context clearly dictates otherwise.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The present disclosure is described in conjunction with the appended figures, which are not necessarily drawn to scale.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

Figure 1:
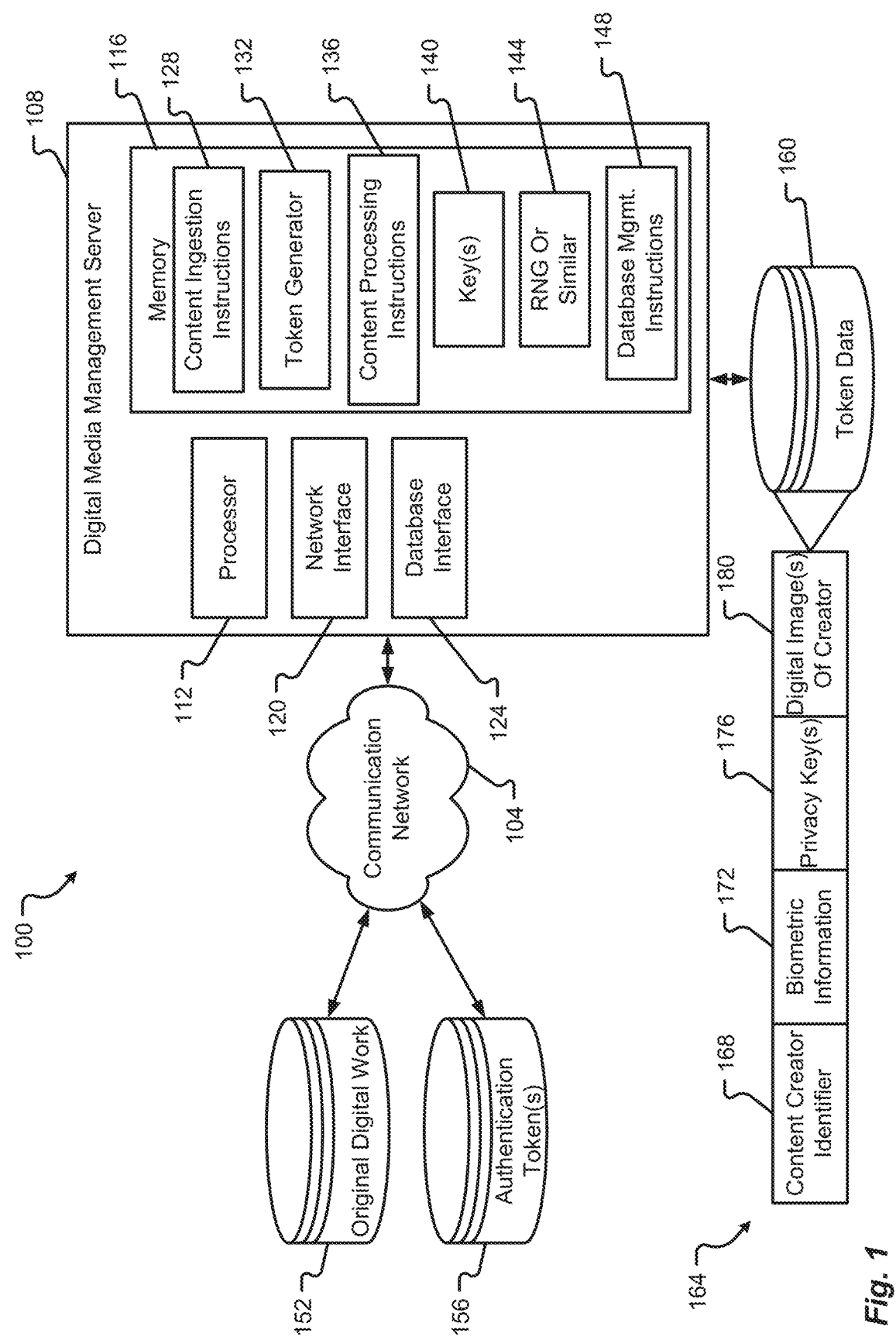
FIG. 1 is a block diagram depicting a system in accordance with at least some embodiments of the present disclosure.

With reference to FIG. 1, an illustrative system 100 will be described in accordance with at least some embodiments of the present disclosure. The system 100, in some embodiments, may include one or more computing devices operating in cooperation with one another to enable the generation and storage of digital authentication tokens as described herein. The components of the system 100 may be utilized to facilitate one, some, or all of the methods described herein or portions thereof without departing from the scope of the present disclosure. Furthermore, although a server is depicted as including particular components or instruction sets, it should be appreciated that embodiments of the present disclosure are not so limited. For instance, the instruction sets of components depicted and described in the server of FIG. 1 may be distributed across multiple servers, computers, cloud systems, or other devices without departing from the scope of the present disclosure. It should also be appreciated that one or more additional servers may be provided with different instruction sets than those depicted in FIG. 1.

The system 100 is shown to include a communication network 104 that facilitates machine-to-machine communications between a digital media management server 108 and/or one or more other network devices. The illustrative server 108 is depicted as a single digital media management server 108, but it should be appreciated that the server 108 or components thereof may be provided in one or many servers and may be distributed across a plurality of servers, for example implementing a server cluster or a cloud-based system (e.g., Amazon's AWS, Microsoft Azure, etc.). While specific capabilities and functional aspects of the server 108 will be described in further detail herein, many details of a digital media management server 108 are described in one or more of the following U.S. Patent Publications, each of which are hereby incorporated herein by reference in their entirety: US 2004/0158731; US 2009/0165128; US 2011/0184791; US 2014/0114675; U.S. Pat. No. 10,050,959; and US 2018/0082043. The various servers described in the applications noted above are configured to store and enable distribution of original digital works and may predicate access to media based on digital rights defined for the media and based on permissions granted to users attempting to view the media. In some embodiments, a server 108 may be configured to have some or all of the functionality described in connection with the servers of the above-noted patent publications. As an example, US 2014/0114675 describes a server or set of servers that are configured to manage health object identifiers (HOIs). The server described in the '675 publication could be configured to provide one or more HOIs to the server 108 as part of the server gathering biometric information for an author or creator of an original digital work. As another example, U.S. Pat. No. 10,050,959 describes a genome-based security device. The techniques of generating and using digital authentication tokens described herein could be combined with the processes described in the '959 patent publication for storing or using synthetic genomic variant-based tokens. As yet another example, US 2018/0082043 describes the systems and methods for tracking biological samples using intrinsic properties where at least some of the intrinsic properties of the sample could be considered representing the sample donor; the author for example. In some embodiments, the server 108 could be configured to gather biometric information for an author or creator of an original digital work using similar intrinsic properties.

The communication network 104 may comprise any type of known communication medium or collection of communication media and may use any type of protocols to transport messages between endpoints. The communication network 104 may include wired and/or wireless communication technologies. The Internet is an example of the communication network 104 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), a Wide Area Network (WAN), a Session Initiation Protocol (SIP) network, a Voice over Internet Protocol (VoIP) network, a cellular network, a peer-to-peer network, a mesh network, and any other type of packet-switched or circuit-switched network known in the art. In addition, it can be appreciated that the communication network 104 need not be limited to any one network type, and instead may be comprised of a number of different networks and/or network types. Moreover, the communication network 104 may comprise a number of different communication media such as coaxial cable, copper cable/wire, fiber-optic cable, antennas for transmitting/receiving wireless messages, and combinations thereof.

Although not depicted, the system 100 may also include one or many client devices that consume or request information from the digital media management server 108. In particular, the digital media management server 108 may include web-based distribution capabilities that enable the distribution, publication, or similar type of online distribution of digital media content from an original digital work database 152 and/or from a database storing authorized modifications of original digital works. The client devices that request and receive such published digital content may correspond to mobile communication devices, Personal Computers (PCs), laptops, tablets, netbooks, and any other type of device that is capable of communicating via the communication network 104. As such, a client device may include one or more network interfaces (e.g., wired interface, wireless interface, etc.) that connect the client device to the communication network 104 and that enable any type of packet-based communication capabilities. A client device may, in some embodiments, be configured for use by a single user or multiple users, depending upon the capabilities of the client device.

The digital media management server 108 is shown to include a processor 112, memory 116, network interface 120, and database interface 124. In some embodiments, the database interface 124 may be provided as a physical set of database links and drivers. Alternatively or additionally, the database interface 124 may be provided as one or more instruction sets in memory 116 that enable the processor 112 to interact with one or more databases 152, 156, and/or 160. As shown in FIG. 1, the digital media management server 108 may be connected with a database 152, 156 via the communication network 104 or the digital media management server 108 may be connected directly with a database 160.

These resources of the server 108 may enable functionality of the server 108 as will be described herein. For instance, the network interface 120 provides the server 108 with the ability to send and receive communication packets over the communication network 104. The network interface 120 may be provided as a network interface card (NIC), a network port, drivers for the same, and the like. Communications between the components of the server 108 and other devices connected to the communication network 104 may all flow through the network interface 120.

The processor 112 may correspond to one or many computer processing devices. For instance, the processor 112 may be provided as silicon, as a Field Programmable Gate Array (FPGA), an Application-Specific Integrated Circuit (ASIC), any other type of Integrated Circuit (IC) chip, a collection of IC chips, or the like. As a more specific example, the processor 112 may be provided as a microprocessor, Central Processing Unit (CPU), Graphical Processing Unit (GPU), Tensor Processing Unit (TPU), or plurality of microprocessors that are configured to execute the instructions sets stored in memory 116. Upon executing the instruction sets stored in memory 116, the processor 112 enables various functions of the server 108.

The memory 116 may include any type of computer memory device or collection of computer memory devices. Non-limiting examples of memory 116 include Random Access Memory (RAM), Read Only Memory (ROM), flash memory, Electronically-Erasable Programmable ROM (EEPROM), Dynamic RAM (DRAM), hard drive, solid state drive, etc. The memory 116 may be configured to store the instruction sets depicted in addition to temporarily storing data for the processor 112 to execute various types of routines or functions.

The illustrative instruction sets that may be stored in memory 116 include, without limitation, a content ingestion instruction set 128, a digital token generator 132, a content processing instruction set 136, a Random Number Generator (RNG) or similar 144, and a database management instruction set 148. In addition to storing instruction sets, the memory 116 may also be configured to store one or more encryption keys 140 that can be used by various instruction sets to encrypt, obfuscate, or otherwise protect any type of data or multiple types of data.

In some embodiments, the content ingestion instruction set 128, when executed by the processor 112, may enable the digital media management server 108 to receive digital content from any number of data sources and prepare such digital content for processing by other instruction sets stored in memory 116. As an example, the content ingestion instruction set 128 may be configured to receive one or more original digital works and/or modified digital works via the communication network 104 via one or more communication packets. In some embodiments the original digital work is a digital representation of an original physical work; a high detailed laser scan and image of a work of art or a statue for example. The content received by the content ingestion instruction set 128 may be received as a file having a predetermined digital format (e.g., a TIFF, JPEG, GIF, PNG, BMP, AVI, FLV, WMV, MOV, MP3, MP4, WAV, WMA, HTML, proprietary formats, custom formats, etc.). Although the examples presented are mainly image and video formats, it should be appreciated that the digital work could represent nearly any modality (e.g., audio, 3D scans, a game, a movie, a sculpture, a person's vital signs, financial data, a book, etc.) Alternatively or additionally, the content received by the content ingestion instruction set 128 may be received as a data stream or other type of packet-based communication. It should be appreciated that the content ingestion instruction set 128 may include a number of different subroutines that are configured to process different types of digital content thereby enabling the digital media management server 108 to process a number of different types of digital works. In some embodiments, the content ingestion instruction set 128 may be configured to receive original digital work from the original digital work database 152. As will be discussed in further detail herein, digital authentication tokens generated based on original digital work and/or based on other information associated with a creator of an original digital work or entity associated with the work may be stored by the server 108 into an authentication token database 156, thereby enabling the digital authentication tokens to be made accessible for use in connection with authorized publications of original digital works from the original digital work database 152. While depicted as separate databases, it should be appreciated that original digital works and authentication tokens can be stored in the same database without departing from the scope of the present disclosure.

The digital content received and processed by the content ingestion instruction set 128 may be provided to the digital token generator 132, the content processing instruction set 136, and any other instruction set stored in memory 116. As can be appreciated, the content processing instruction set 136 may be configured to process original digital works or authorized modifications thereof and, in some embodiments, may be configured to process original digital works in connection with authentication tokens in a way that enables the authenticity and provenance of original digital work to be validated. The content processing instruction set 136 may also be configured to combine or connect a digital authentication token with original digital work.

The digital token generator 132, when executed by the processor 112, may enable the digital media management server 108 to generate one or more digital authentication tokens. As will be described in further detail herein, the digital token generator 132 may be configured to generate a number of different types of digital authentication tokens which can be attached to, incorporated in, or otherwise used to prove an authenticity of digital work, whether original digital work or an authorized modification of the original digital work. Further capabilities of the digital token generator 132 will be described below. Although the authentication token is referred to as a digital authentication token, one should appreciate the digital authentication token can be physical manifested. For example, the digital authentication token could be printed on a paper media, 3D printed, sculpted, or otherwise converted to a physical media.

In some embodiments, the various instruction sets (e.g., digital token generator 132 and/or content processing instruction set 136) may be configured to use one or more keys 140 and an RNG or similar 144 type of computing mechanism. Specifically, the digital token generator 132 may be configured to utilize one or more encryption keys 140 as part of generating a digital authentication token. Alternatively or additionally, the key(s) 140 may be used by the content processing instruction set 136 as part of generating an obfuscated or virtual set of biometric information for a user that is ultimately leveraged as part of generating a digital authentication token. The RNG or similar 144 may include any type of processing routine that generates a random, pseudorandom, or deterministic output. In some embodiments, the RNG or similar 144 may include a random number generator, a pseudorandom number generator (PRNG), a rolling code generator, hash-based RNG, or a combination thereof. The RNG, in some embodiments, can include a deterministic RNG algorithm or technique that uses an initial seed to generate a series of random numbers. Such algorithms can be implemented in software or hardware, or a combination of both. The advantage of using a deterministic RNG algorithm leveraging a seed provides the ability to reproduce a series of random numbers at a later time to validate authenticity of the original work via the digital authentication token.

The database management instruction set 148, when executed by the processor 112, may enable the digital media management server 108 to interface with the various databases 152, 156, 160, generate database queries, receive responses to database queries, write new entries to databases, modify database entries, and the like. In some embodiments, the database management instruction set 148 is configured to manage information maintained in each of the databases. In other embodiments, the database management instruction set 148 may include different subroutines, each being used to manage a different database. In some embodiments, the database management instruction set 148 may be configured to manage data 164 stored in the token database 160, which is ultimately used by the digital token generator 132 to generate digital authentication tokens or other types of tokens for use in digital content authentication and/or verification.

The data 164 stored in the token database 160 may include a number of data fields used to store different types of data that can ultimately be used to generate a digital authentication token, generate a virtual sequence, or generate other types of data/files that can help ensure an authenticity or provenance of digital content. Illustrative data fields or types of data that may be maintained in the data 164 include, without limitation, a content creator identifier field 168, a biometric information field 172, a privacy key field 176, and a digital image(s) of a creator field 180. One or more of these fields may simply store data whereas other fields may be used to store files or links to data files. In some embodiments, the content creator identifier field 168 may be used to store information that uniquely or substantially uniquely identifies a creator of a digital work. Examples of information that can be stored in the content creator identifier field 168 include, without limitation, creator name, creator address, a unique identification number assigned to the creator, a username, a nickname, an email address, or any other collection of alphanumeric characters that describe or can be used to identify a person, which may correspond to a creator, editor, publisher, or other individual/corporation involved with the production/publication of digital works.

The biometric information field 172 may be used to store various types of biometric information or intrinsic properties associated with or descriptive of a person. In some embodiments, the biometric information field 172 may store one or more data files that contain DNA sequence, or other omic sequence, information of a person. The data file(s) may or may not be encrypted with a privacy key 176 for privacy protection. Other non-limiting examples of the types of information or data files that may be stored as biometric information 172 include iris information, facial feature information, fingerprint information, ear print information, DNA sequence information, portions of DNA sequence information, RNA sequence information, biometric templates, expressed protein information, mutations, or combinations thereof.

The digital image(s) field 180 may be used to store one or more files that contain one or multiple images of a creator or images that are associated with a creator. In some embodiments, the image files may include one or more of a TIFF, JPEG, GIF, PNG, BMP, or the like. Alternatively or additionally, the digital image(s) may include motion images, a plurality of images, or video files. As will be discussed in further detail herein, the various files and/or information contained in the database 160 can be used by instruction set(s) of the digital media management server 108 in connection with producing authenticated and verifiable digital works.

Figure 2:
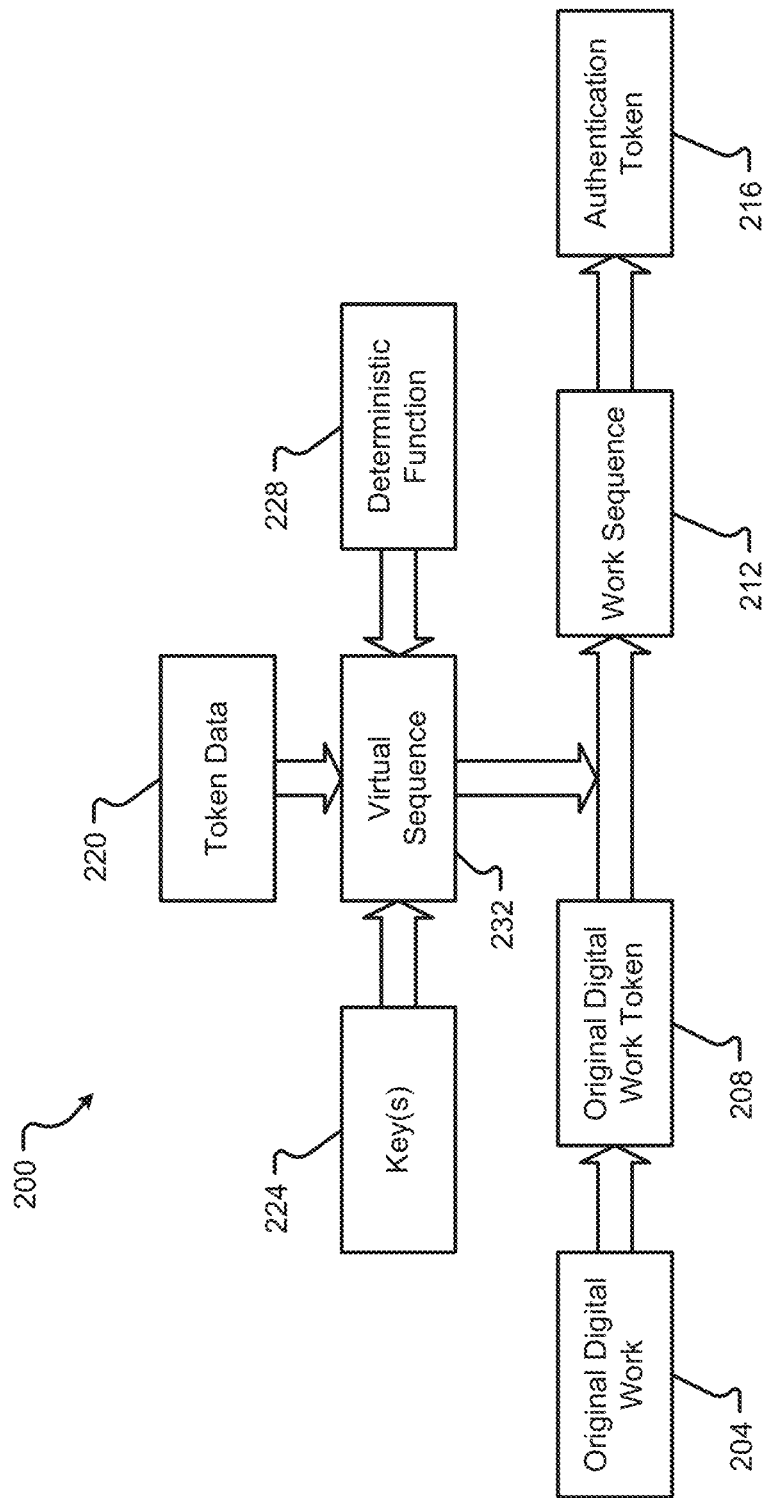
FIG. 2 is a block diagram depicting a data flow in accordance with at least some embodiments of the present disclosure.
Figure 3:
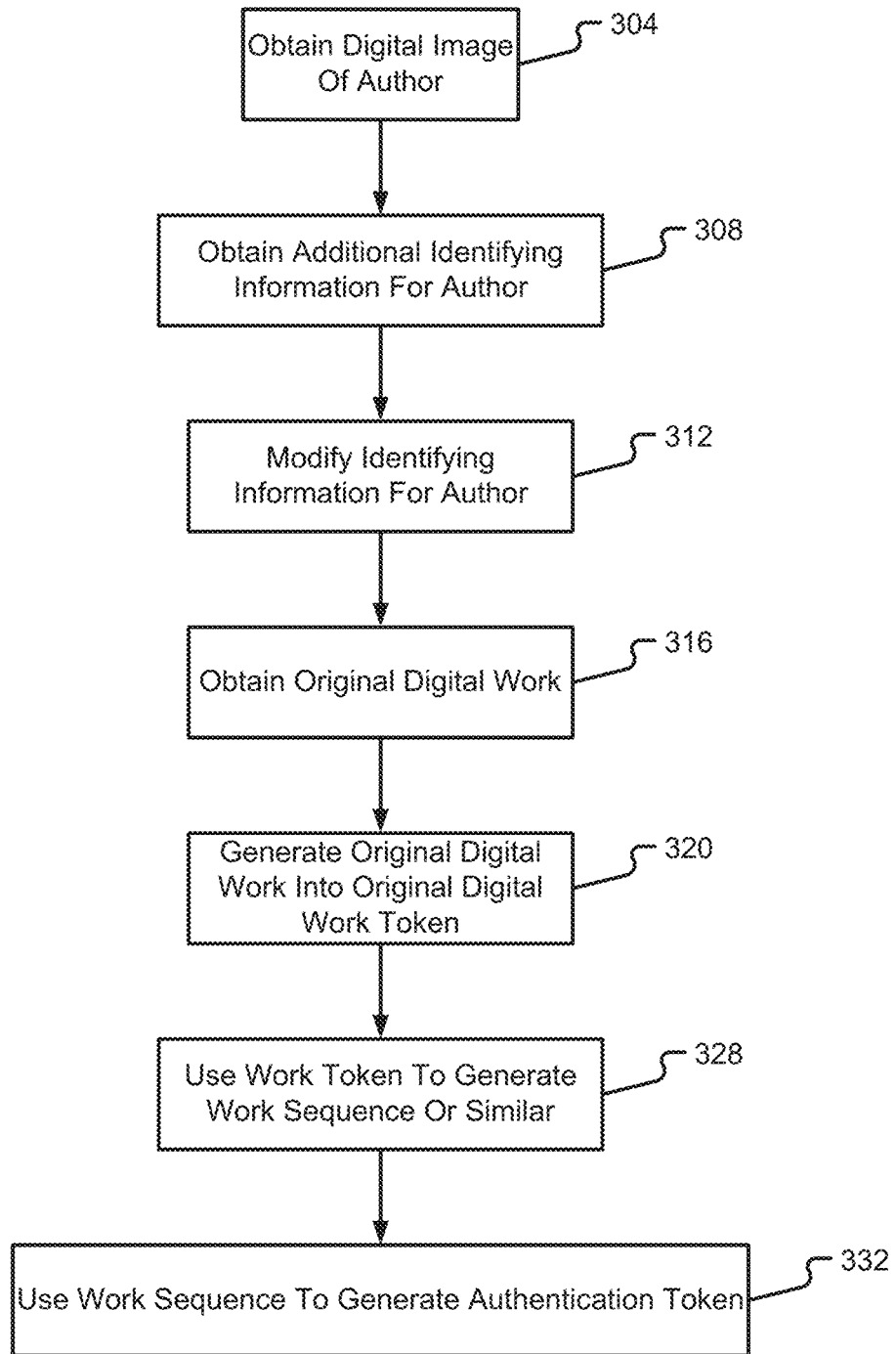
FIG. 3 is a flow chart depicting a method of processing digital content in accordance with at least some embodiments of the present disclosure.

With reference now to FIGS. 2 and 3, a first method of processing one or more original digital works in connection with generating an authentication token will be described in accordance with at least some embodiments of the present disclosure. The method begins by obtaining a digital image or multiple digital images of an author or creator of a digital work (step 304) or other desired images. In some embodiments, the image of the creator may correspond to token data 220 that is retrieved from the token database 160. Other types of token data 220 that may be retrieved from the database 160 by the database management instruction set 148 include, without limitation, the digital content or metadata of digital work produced by the author, an external notarization token (e.g., a blockchain hash, a distributed ledger token, a certification token, etc.), a timestamp (e.g., a time when the information is retrieved from the database 160 or a time when the information was written to the database 160), a location, or other factors.

The method continues by obtaining additional identifying information for the author (step 308). This additional identifying information may also be considered token data 220 and may include, for instance, an author's biometric (e.g., iris information, DNA sequence information, portions of DNA sequence information, RNA information, fingerprint, etc.), encrypted versions of the author's biometric, templates of the author's biometric, or combinations thereof. In some embodiments, both the digital image and the additional identifying information for the author may be retrieved substantially simultaneously with a single database query formed using the database management instruction set 148.

The method continues with the digital token generator 132 modifying at least some of the identifying information for the author (step 312). In some embodiments, the modifications made to the identifying information may result in the creation of a virtual sequence 232 (e.g., if the identifying information retrieved in step 308 included DNA sequence information. In other embodiments, the manner in which the identifying information is modified may depend upon the format of the identifying information and whether such information would release personal or private data about the author. Such information may or may not be encrypted prior to being modified. Virtual sequence 232 can be constructed to ensure privacy of the author.

In some embodiments, as shown in FIG. 2, the virtual sequence 232 may be produced using a deterministic function 228 and one or more encryption keys 224. For instance, a deterministic function 228, such as a hash function or similar one-way algorithmic function (e.g., RNG, PRNG, etc.), may be used to determine which portions of the identifying data should be modified as part of generating the virtual sequence 232. The key(s) 224 may be used to encrypt or hide some or all of the virtual sequence. The key(s) 224 may correspond to one or more private encryption keys that belong to a private/private key pair or a private/public key pair. The private encryption key(s) may correspond to encryption keys that are only known or delivered to a communication device owned/operated by the author.

The method may then continue with the content ingestion instruction set 128 obtaining the original digital work 204 that is to have a digital authentication token applied thereto or combined therewith (step 316). The original digital work 204 may be retrieved from the original digital work database 152 and/or may be received via a data stream. In some embodiments, the original digital work 204 may correspond to one or several electronic files that produce the author's creative work when rendered on a client computing device (e.g., a mobile communication device, laptop, PC, tablet, etc.). Original digital work 204 can take on different forms or modalities including image data, text data, 3D rendering data, scanned data, video data, audio data, or other types of data.

The original digital work 204 may then be converted into an original digital work token 208 by the digital token generator 132 (step 320). In some embodiments, the original digital work token 208 may correspond to a hash value or similar output of a deterministic function. The digital token generator 132 may then use the original digital work token 208 in combination with the virtual sequence 232 to generate a work sequence 212 (step 328). As can be appreciated, the work sequence 212 may or may not have a structure similar to a DNA sequence, depending upon the nature of the token data 220 and, specifically, the identifying information obtained for the author in step 308. Thus, the work sequence 212 may only correspond to data structure having a DNA sequence format if the identifying information obtained in step 308 corresponded to a DNA sequence or portion thereof. If the identifying information obtained in step 308 corresponded to a different type of data (e.g., a template for a fingerprint or retina), then the work sequence 212 may have a similar format to the template for the fingerprint or retina.

The work sequence 212 may then be used to generate an authentication token 216 (step 332). This authentication token 216 may correspond to a digital token that can be image-based. In some embodiments, the authentication token 216 may be stored in the authentication token database 156 as an image-based electronic file for later use in connection with authorized publications of the original digital work 204 or authorized modifications thereof. Specifically, the authentication token 216 may be attached, affixed, or used to modify original digital works during an authorized publication of the original digital work. The presence of the digital authentication token 216 in combination with the original digital work may allow a viewer of the publication of the original digital work to confirm and trust that the original digital work is both authentic and has a verified provenance. A published version of the original digital work without the digital authentication token produced as described herein may correspond to a counterfeit or untrusted version of the digital work. Thus, the digital authentication token creates a mechanism for binding the author's/creator's identity directly to the original digital work produced by the author in a way that is easily and quickly verifiable by a viewer/consumer of the published digital work.

Figure 4:
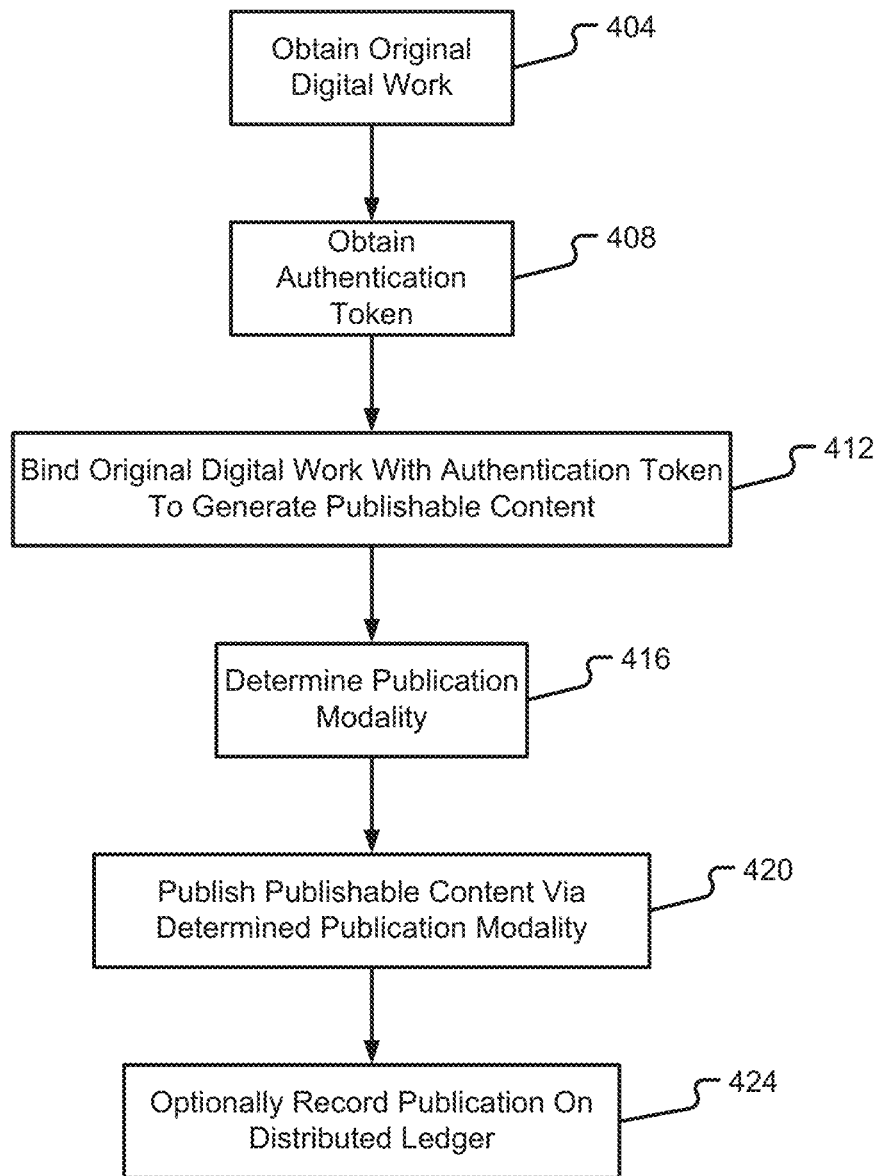
FIG. 4 is a flow chart depicting a publication method in accordance with at least some embodiments of the present disclosure.

With reference now to FIG. 4, a method of publishing digital works will be described in accordance with at least some embodiments of the present disclosure. The method begins with the digital media management server 108 obtaining original digital work (step 404). The original digital work may be received from the original digital work database 152 using a database query or data request. Alternatively, the original digital work may be pushed to the digital media management server 108 with an instruction to publish the original digital work or make the original digital work available for public consumption (e.g., retrieval by a client device).

The method proceeds with the content processing instruction set 136 obtaining one or more authentication tokens 216 for use in connection with the publication of the original digital work 204 (step 408). In some embodiments, the authentication token 216 obtained in this step may correspond to a digital authentication token that was generated by the digital token generator 132 and the token may be received directly from the digital token generator 132 or from the database 156. In some embodiments, the authentication token 216 selected/retrieved from the database 156 may correspond to a particular authentication token 216 that is associated with a creator of the original digital work 204. For instance, a creator of the original digital work 204 may have their own unique individual authentication token 216 or unique set of authentication tokens 216 that are used for publication of their original digital works 204. Thus, the authentication token 216 may be selected based on the creator of the original digital work 204, a publisher of the original digital work 204, an editor of the original digital work 204, or a combination thereof.

The content processing instruction set 136 may then bind the original digital work 204 with the authentication token 216 to generate publishable content (step 412). In some embodiments where the digital authentication token 216 that was generated by the digital token generator, the binding may include attaching the digital authentication token 216 to the original digital work 204, appending the digital authentication token 216 with the original digital work 204, including the digital authentication token 216 in a presentation of the original digital work 204, rendering token 216 with work 204, providing a link to the digital authentication token 216 via a presentation of the original digital work 204, modifying a portion of the original digital work 204 with the digital authentication token 216, or combinations thereof.

The method may then proceed by determining a publication modality or channel (step 416). In some embodiments, the original digital work 204 may be published by a plurality of different modalities or channels, in which case the determination of step 416 may result in determining each/all of the publication modalities. Examples of publication modalities include, without limitation, web-based publication modalities (e.g., inclusion as a page or portion of a website), social media-based publication modalities (e.g., inclusion as a link within a social media feed, published with a post on the social media feed, etc.), broadcast publication modalities, video publication, print publication, audio publication, or combinations thereof.

The method then continues with the content processing instruction set 136 publishing the publishable content via the determination publication modality(ies) (step 420). This step may include pushing the publishable content (e.g., the combination of the original digital work 204 with the digital authentication token 216) via one, some, or all of the determined modalities. In some embodiments, the manner in which the publishable content is generated (e.g., the way in which the original digital work 204 is modified or presented with the digital authentication token 216) may depend upon the nature of the digital authentication token 216 as well as the determined publication modality.

The method may also include a step in which the content processing instruction set 136 causes the publication of the publishable content to be recorded on a notarized or distributed ledger (step 424). Recordation of the publication event may include updating the distributed ledger (e.g., Openchain, Hyperledger, Ethereum, bitcoin, hashgraph, IOTA, TRON, etc.) with information about the publication, information about the original digital work 204, information about the digital authentication token 216, linking the information to an entry in the digital ledger that has already been verified by a participant to the distributed ledger, timestamping the distributed ledger with a date of the publication or a date on which the original digital work 204 was produced, or combinations thereof. One should appreciate that a distributed ledger is a type of notarized ledger where contents are stored such that the data can be notarized through various techniques. Example techniques include building a consensus of distributed peer, hashing the content with another ledger's information (e.g., hash value of a current block), combining the content with a certificate from a certificate authority, or other notarization approach.

Figure 5:
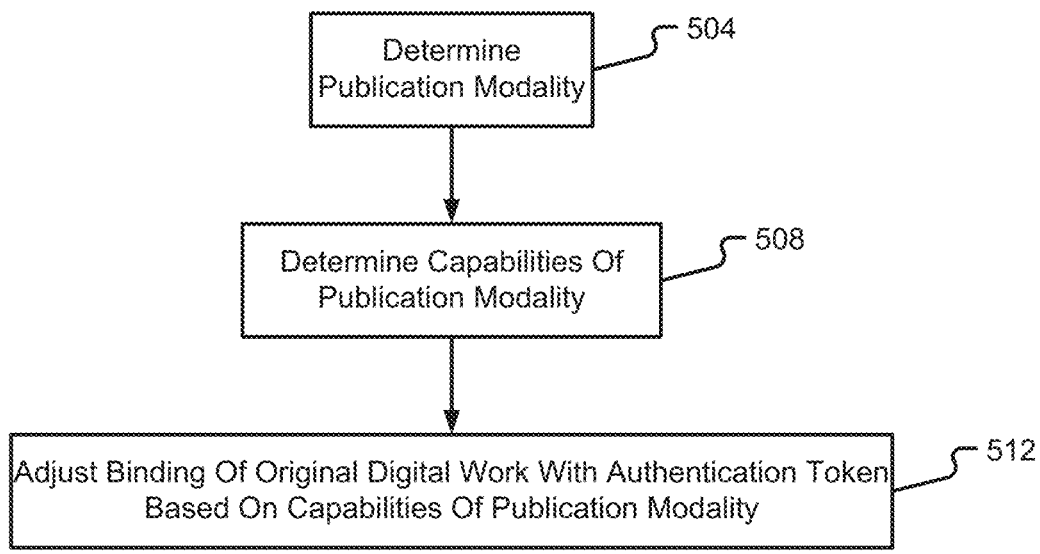
FIG. 5 is a flow chart depicting a method of binding original digital content with modified digital content in accordance with embodiments of the present disclosure.

With reference now to FIG. 5, additional details of a publication method will be described in accordance with at least some embodiments of the present disclosure. The method begins with the content processing instruction set 136 determining the publication modality (step 504). This particular step may be similar or identical to step 416.

The method continues with the content processing instruction set 136 determining capabilities of the publication modality (step 508). Capabilities of the publication modality may include media types that can or cannot be presented via the publication modality, a resolution of presentation via the publication modality, whether the publication modality is capable of presenting static or dynamic content, and combinations thereof.

Based on the capabilities of the publication modality, the content processing instruction set 136 may then adjust the manner in which the original digital work 204 is bound with the digital authentication token 216 (e.g., into the publishable content) (step 512). In some embodiments, the content processing instruction set 136 may adjust a font or element size/shape/type/color of elements of the digital authentication token 216 based on the resolution or pixel size used for the publication modality. In some embodiments, the content processing instruction set 136 may determine whether to use a dynamic or static digital authentication token based on whether the publication modality is capable of presenting or otherwise rendering dynamic media content or not. In some embodiments, if the publication modality is capable of providing audible content, then the binding of the original digital content with the digital authentication token may include an audible element (e.g., a hyperlink may be provided in the original digital content that, when clicked, causes a computing device to play an audible message spoken by the author/including a voiceprint of the author). It should be appreciated that other variations of adjustments can be made in step 512 without departing from the scope of the present disclosure.

Figure 6:
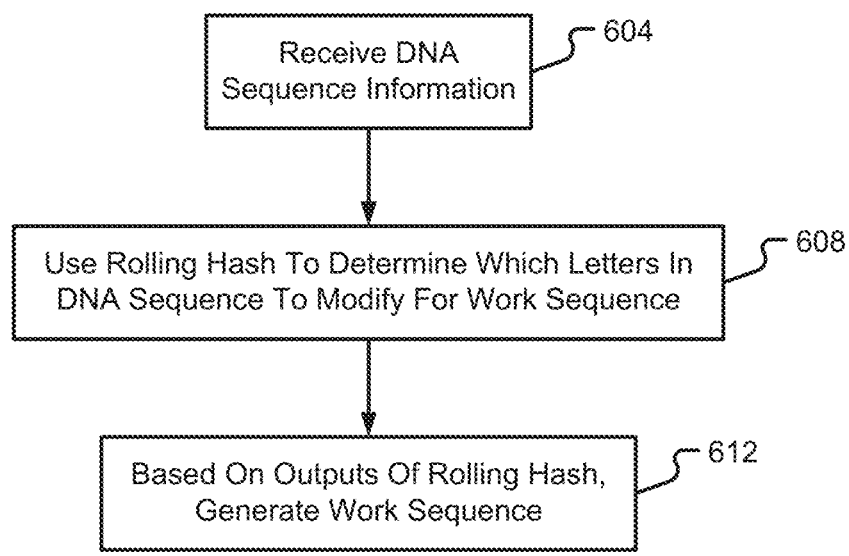
FIG. 6 is a flow chart depicting a method of generating a work sequence in accordance with embodiments of the present disclosure.

With reference now to FIG. 6, additional details regarding the production of a work sequence 212 will be described in accordance with at least some embodiments of the present disclosure. The method begins when DNA sequence information is received at the digital token generator 132 (step 604). The DNA sequence information may include a full sequence listing or a portion of a sequence listing. In some embodiments, the DNA sequence information may include one or more of introns, exons, WGS, SNPs, INDELs, rearrangements, transcription profiles, known proteomic mutations, tissue of origin, differences between tissue sequences (e.g., tumor vs. normal, a first tissue type vs. a second tissue type, tissue vs. reference, etc.), or many other flavors of DNA.

The method may proceed with the digital token generator 132 employing a rolling hash (e.g., using a current hash as a seed for the next hash, using a random number as a seed to generate a new number, etc.) to determine which letters in the DNA sequence information to modify for the work sequence 212 (step 608). In some embodiments, the rolling hash may include a deterministic selection of a particular hash function, a utilization of a particular and rotating seed value, or the like. One should appreciate that the hash value from a rolling hash can be used as a deterministic PRNG. For example, one or more bytes from the hash value can be examined and used as a pseudo-random number.

Based on the outputs of the rolling hash, the digital token generator 132 may generate the work sequence 212, which effectively represents an obfuscated version of the DNA sequence information received in step 604 (step 612). If a one-way hash is used as part of this step, then the DNA sequence information can be protected from disclosure or unwanted distribution to untrusted entities. In some embodiments, the work sequence 212 may be used to replace one or more elements of an image (e.g., pixels). As a non-limiting example, one, some, or all pixels of an image of an author of a creative work may be replaced with letters from the work sequence 212 in a systematic fashion, thereby creating a binding between the author's biometric information (e.g., DNA sequence information) and the image of the author. This modified image of the author can then be used to secure or prove an authenticity of a creative work prepared by the author or the modified image of the author may correspond to the creative work itself.

Figure 7:
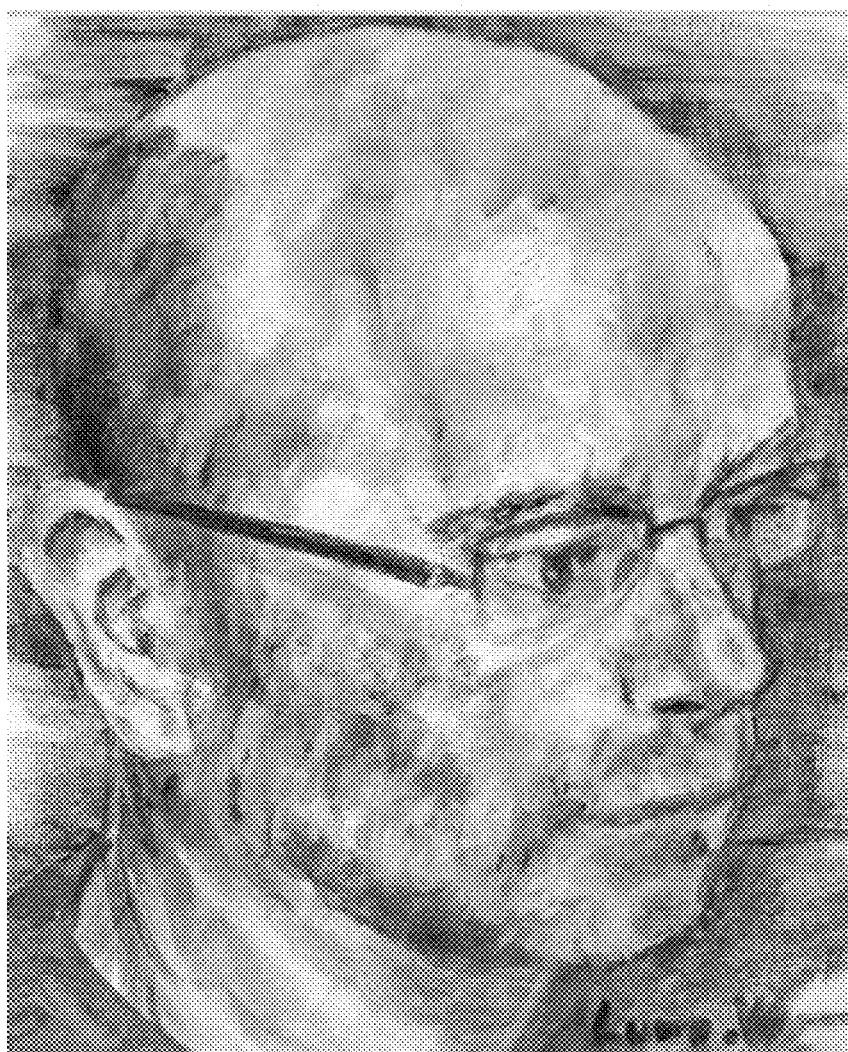
FIG. 7 illustrates an example of an image in accordance with embodiments of the present disclosure.
Figure 8:
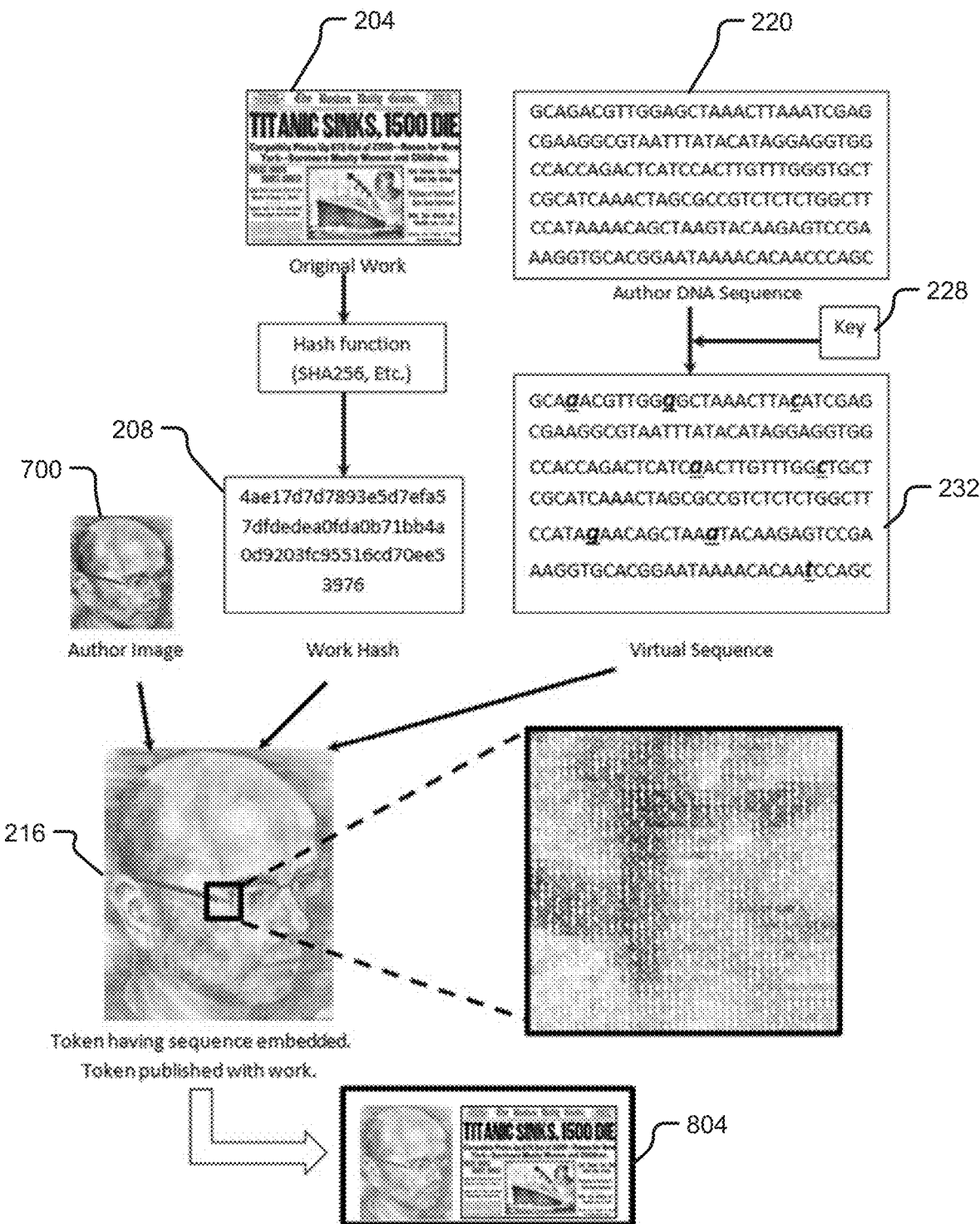
FIG. 8 illustrates a process to generate a digital authentication token in accordance with embodiments of the present disclosure.
Figure 9:
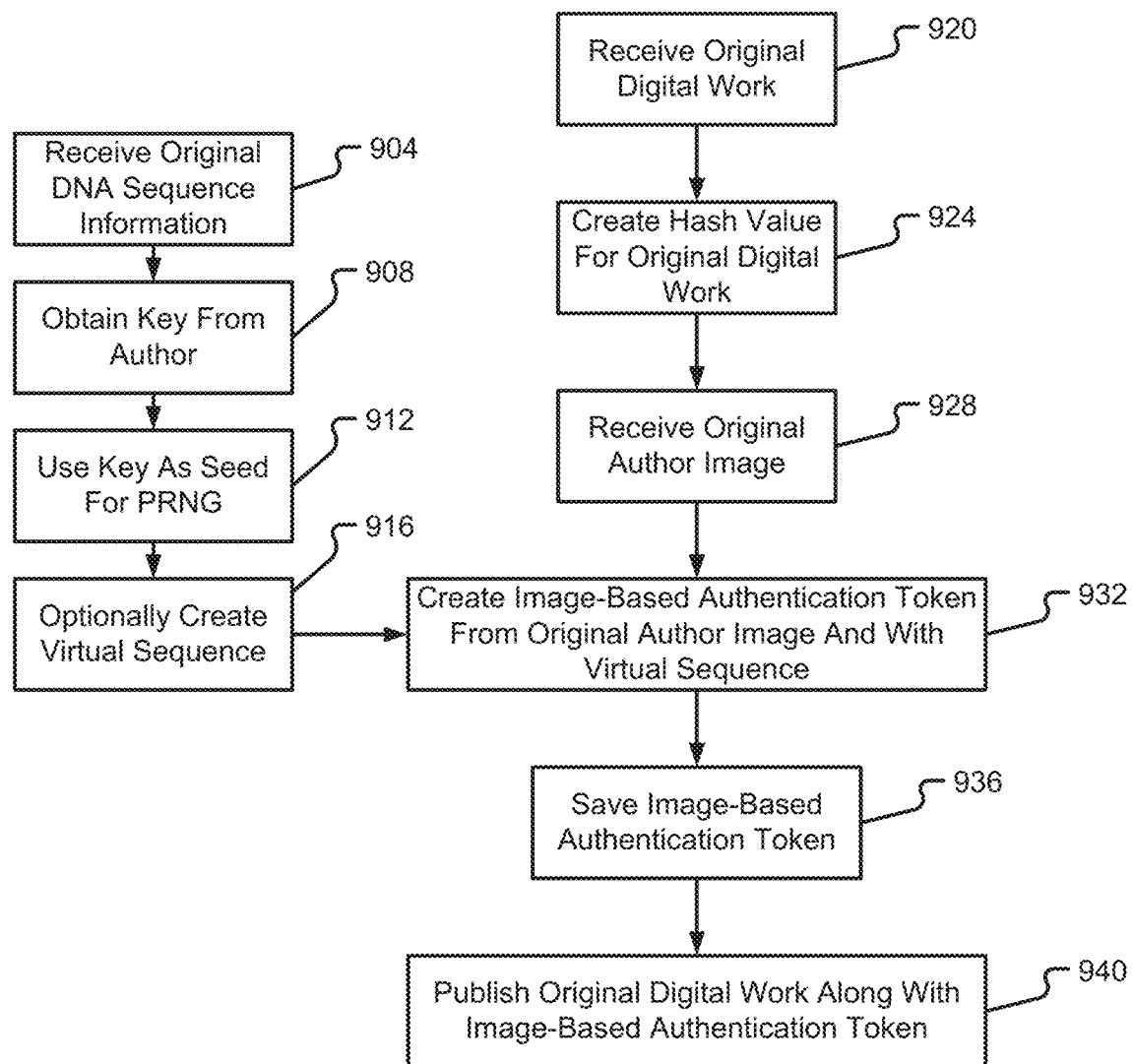
FIG. 9 illustrates a flow chart for generating a digital authentication token as shown in FIG. 8.

With reference now to FIGS. 7-9, another method of producing a digital authentication token and using the token in connection with an authorized publication of an original digital work 204 will be described in accordance with at least some embodiments of the present disclosure.

FIG. 7 illustrates an example of an author image 700 that may include one or multiple digital images. In some embodiments, the image 700 may correspond to a photographic image whereas in other embodiments the image may correspond to a painted (as shown) or hand-drawn image. Alternatively or additionally, the author image 700 may correspond to an example of an original digital work 204 that will also be published in connection with an authentication token 216 generated as described herein. In other embodiments, the author image 700 may be different from the image of a creator of the original work that is used in connection with generating an authentication token.

The method may begin with the server 108 receiving original DNA sequence information or other types of token data 164 from the token database 160 (step 904). The original DNA sequence information may, optionally, be obfuscated using a key/seed and a deterministic function to create the virtual sequence (step 908). As discussed above, the virtual sequence may be used to protect the privacy of the creator of the original digital work and their actual DNA sequence information.

In the example of FIGS. 8 and 9, consider the news story an example of original digital work 204. The original digital work 204 may be received (step 920) at the server 108 in parallel with receipt of the original DNA sequence information in step 904, before step 904, or after step 904. The original digital work 204 may correspond to the content that will eventually be published along with an authentication token 216. In some embodiments, the original digital work 204 may be run through a hash algorithm (or similar one-way function) to create a hash value (e.g., an original digital work token 208) for the original digital work 204.

The method may then continue by receiving an image 700 of the author, which may or may not also correspond to the original digital work 204 (step 928). The image 700 may be received in one or more electronic files that are formatted to store digital images.

Referring back to step 904, after the DNA sequence information (e.g., token data 220) is received, the method may continue by obtaining an encryption key (e.g., a private encryption key) from the author or on behalf of the author (step 908) and then using the key as a seed for a PRNG (step 912). The deterministic PRNG may then be used to modify the original DNA sequence information with some probability to form the virtual sequence 232 (step 916). For example, the probability might result in 10%, 20%, 50%, or other percentage of the original DNA sequence to change to form virtual sequence 232.

From the image 700 of the author and the virtual sequence 232, an image-based digital authentication token 216 may be generated (step 932). In some embodiments, the digital authentication token 216 is generated by processing the image 700 of the author on a pixel-by-pixel basis. In some embodiments, the hash value of the original digital work 204 is used as a seed for a deterministic PRNG. Then for each pixel of the image 700, a pixel color is determined or identified and a letter is read from the virtual sequence 232. Based on the output of the deterministic PRNG, then the token generator 132 may determine if the letter from the virtual sequence 232 should change. One should appreciate this change could further change virtual DNA sequence as represented in the token. If it is determined that the letter should change, then a new, different, letter is picked (again using the PRNG) thereby further securing privacy of the original DNA sequence information as well as introducing additional factors for authenticity. The selected letter or the new replacement letter thereof is then inserted into a pixel location with a color that is substantially or identically the same as the color of the pixel being replaced by the letter. This process is continued until all desired pixels (e.g., one, some, or all pixels) of the image 700 have been replaced with a corresponding letter having a color selected based on the color of the pixel being replaced and having a size selected based on the size of the pixel. The resulting output of the pixel-by-pixel processing of the image 700 may correspond to the digital authentication token 216. It is also contemplated that the color of the letters/pixels could also be changed according to a deterministic function. However, it would be desirable to retain substantially the same hue to maintain visual integrity of the original image.

As shown in FIG. 8, each pixel of the image 700 may be replaced with letters from a DNA sequence or virtual sequence 232. It should be appreciated that the letters may be obtained directly from DNA sequence information or from an obfuscation thereof (e.g., the virtual sequence 232). FIG. 8 depicts an exploded portion of the image 700 and the letters that are eventually used to replace pixels of the image 700, thereby forming the digital authentication token 216. In some embodiments, the letters may have their size modified to accommodate the size of the pixels from the image 700 and may further have the color modified to try and match a color of the pixel being replaced by the letter. Thus, a set of modified letters representing a combination of the DNA sequence information (or virtual sequence 232) and the image 700 are used to generate a final digital authentication token 216. In some embodiments, letters from the DNA sequence information may be modified to the virtual sequence 232 based on the deterministic function using pixel information and probability as an input.

The digital authentication token 216 may then be stored in the authentication token database 156 (step 936). The digital authentication token 216 may be stored in a read only format and may be stored as a text file, an image file, a picture file, a movie file, or other suitable digital formats. The stored digital authentication token 216 may then be used as part of publishing the original digital work 204 (step 940). The published content 804 may correspond to a combination of the digital authentication token 216 and the original digital content 204.

In some embodiments, the system 100 described herein may be provide a for-fee service to generate digital authentication tokens 216 for other producers of original digital content 204 that desire to control the manner in which their original digital content 204 is published/distributed. In other words, the entity operating the server 108 may simply correspond to an entity that generates storable and useable authentication tokens 216 and the entity does not necessarily need to correspond to an entity that publishes the original digital content 204.

Additionally, the system 100 described herein may include one or more components for validating original digital works 204 and/or for validating publications of original digital works 204 and authentication tokens 216 published in connection therewith. This validation service may or may not be considered a certification entity, such as a certificate authority used to validate distributions of web-based content. The components of the server 108 used to generate a digital authentication token 216 may also be configured to receive tokens and validate those tokens against one or more tokens stored in the authentication token database 156. In this way, the entity operating the server 108 may provide a validation function for consumers of original digital works 204. For example, a published digital work can be compared with the corresponding token. If the verification systems discovers that token does not carry the proper deterministic features of the published digital work, then the published digital work is suspect.

There are multiple features by which the verification system can determine if the token/work pair is a valid pair. In some embodiments, the verification system can use image recognition algorithms to determine if the token has recognized or recognizable features. Example algorithms include SIFT, TILT, DAISY, edges detection algorithms, or other algorithms. OpenCV (see URL www.opencv.org) offers access to implementations of various image processing algorithms that can be leveraged in support of verification techniques. Such techniques allow a computing system execute implementations of the recognition algorithms on the original work or authentication token to obtain corresponding recognition descriptors. The descriptors can then be used as an index into a database to retrieve information related to the original work or token. In some embodiments, the database operates as Knn nearest neighbor search tree. Thus, the system is object to look up related information about the original work, including a copy or archived version of the original work and corresponding authentication token, which can be compared to the published version to determine if they are sufficiently similar.

Yet further, the digital token can be analyzed via optical character recognition (OCR) to pull out the corresponding sequence information embedded in the token. The extracted sequence information can be compared to the known virtual sequences for one or more author/work pairs. Still further, the published digital work can be run through the same hash algorithm used to create the token in the first place. If the resulting hash value can be used to reproduce the token, then the work is likely valid. Still further, the published token and the verification token can be compared at the pixel level, sequence level, or even algorithm descriptor level as referenced above. Should the two tokens match within a threshold distance or other criteria, then the work/token pair is valid where the distance can be calculated as a sum over the absolute value of the differences between the various elements of the token (e.g., pixels, sequence letters, descriptors, etc.).

In some embodiments, differences between a verification token and a published token can be calculated using or more techniques. As alluded to previously, the similarity (or difference) can be measured by comparing colors on a pixel by pixel basis in an RGB space. The difference between two pixels can be measured using a Euclidian distance metric such as: $\text{Diff}_{VP}=\text{SQRT}((R_V-R_P)^2+(G_V-G_P)^2+(B_V-B_P)^2)$ where a first pixel ($P_V$) from the verification token has an RGB value of ($R_V$, $G_V$, $B_V$) and the corresponding pixel (Pp) from the published token has an RGB value of ($R_P$, $G_P$, $B_P$). One type of difference metric between tokens can then be the sum of differences for all pixels: Token difference metric=$\Sigma\text{Diff}_{VP}$. Naturally, this assumes there is a one to one correspondence of pixels in the two tokens. In some embodiments, the calculation can be weighted or adjusted based on differing attributes (e.g., size, shape, aspect ratio, etc.) between tokens by conducting one or more affine or other transformations to ensure the two token are equivalent to a desired degree.

In other embodiments, the differences can be measured based on actual image recognition algorithm descriptors using a similar calculation. For example, in some cases a SIFT descriptor can have 128 dimensions where RGB values only have 3. Further, rather than using all descriptors resulting from an image analysis, it is possible to use a subset, say 10, 20, 100, or other number of most similar descriptors. This approach can be advantageous when the validation or verification system lacks complete fidelity to capture the published work token. Thus, this type of validation or verification might be best used on mobile platforms (e.g., cell phones, webcams, etc.).

Still further embodiments including conducting OCR analysis as suggested above and comparing the verification token to the published token. Each letter in the sequences can be compared. The difference between the tokens can be measured using a Hamming distance (e.g., the number of differences found). Alternatively, the difference could be measured by assigning values to each observed letter (e.g., A=1, T=2, C=3, G=4) and then summing over the absolute values of the differences. One should appreciate that other sequences beyond DNA are contemplated and could include RNA (i.e., AUGC), amino acids (i.e., AGILPVFWYDER-HKSTCMNQ), or other letters or symbols representing omic information.

Yet further, multiple differences can be combined to form a single validation or verification score. Using the previous metrics, a validation or verification score can be calculated by normalizing the difference metrics for pixel-to-pixel comparison, descriptor comparisons, OCR comparisons, or other difference metrics. The normalized metrics can then be summed, possibly including weights, to arrive at the final verification score. If the final verification or validation score satisfies the verification or validation criteria (e.g., greater than a threshold value, lower than a threshold value, author specific criteria, security criteria, HIPAA requirements, etc.), then the published work-token pair can be considered valid. One should appreciate that validation or verification scores can also be multi-valued rather than single valued.

Figure 10:
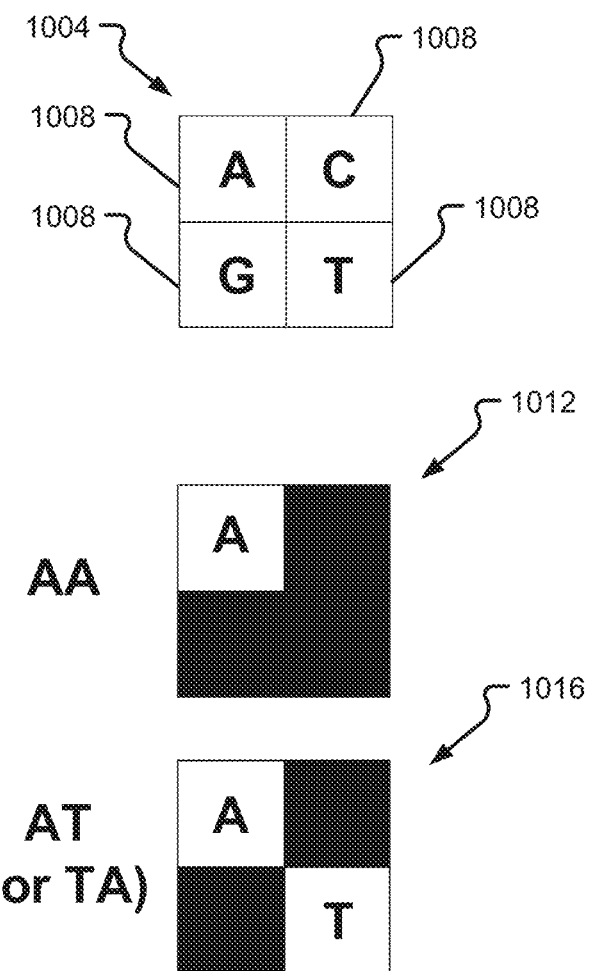
FIG. 10 illustrates components of an example genotype pixel and variants thereof in accordance with embodiments of the present disclosure.

Referring now to FIGS. 10-22, additional embodiments related to the use of pixels, as described herein, as part of a pixel group. A specific pixel group depicted and described herein is a genotype pixel 1004, which is depicted in FIG. 10. It should be appreciated that a genotype pixel is one of many possible pixel groups encodings that may be used in accordance with at least some embodiments of the present disclosure. The use of a genotype pixel 1004 is particularly useful, however, because certain information known about possible genotype and impossible genotypes may be used to determine allowable genotype pixels and forbidden genotype pixels as will be discussed in further detail herein.

In the depicted embodiment of FIG. 10, a genotype pixel 1004 is shown to include a number of subpixels 1008. Each subpixel may correspond to one physical pixel of an image capture device, one physical pixel of an image display device, one pixel of published content, one pixel of published content that is rendered via a display screen, a collection of physical pixels of an image capture device, a collection of physical pixels of an image display device, a collection of pixels of published content, or a collection of pixels of published content that are rendered via a display screen. In other words, a subpixel 1008 of a genotype pixel 1004 may have a 1:1 correspondence with a pixel used to present or capture published content or there may be a one-to-many correspondence.

FIG. 10 further illustrates the construction of a genotype pixel 1004 may be organized based on information known, a priori, about a genotype and how an individual genotype can be represented. Although illustrated as a 2×2 collection of subpixels 1008, a genotype pixel 1004 may correspond to a 2×2 square, a 4×1 rectangle, or a 1×4 rectangle. Moreover, if subpixels 1008 are organized according to some other data scheme (e.g., to represent something other than a genotype), then a greater or lesser number of subpixels 1008 may be used to form a pixel group. Said another way, a genotype pixel 1004 should be construed as a non-limiting example of a pixel group and different types of pixel groups may have more or less than four subpixels 1008 without departing from the scope of the present disclosure. For example, in embodiments where the 20 amino acids are used, a pixel group might be 5×5 arrangement thereby covering all 20 amino acids while also having forbidden arrangements as discussed below.

One specific example of a genotype pixel 1004 is a homozygous genotype pixel 1012. A homozygous genotype pixel 1012, in the depicted embodiment, has one subpixel 1008 of one value (e.g., a white color) whereas all other subpixels 1008 have another value (e.g., a black color). Another specific example of a genotype pixel 1004 is a heterozygous genotype pixel 1016. A heterozygous genotype pixel 1016, in the depicted embodiment, has two subpixels 1008 of one value (e.g., a white color) whereas two other subpixels 1008 have another value (e.g., a black color). It should be appreciated that each subpixel 1008 may be assigned any color, brightness, color saturation, etc. to correspond to the associated presence of the nucleotide (e.g., A, C, G, T). Thus, presence of a particular nucleotide may be represented with a particular subpixel 1008 using a white/black value for the subpixel 1008, using other colors for the subpixel 1008, using magnetic encoding for the subpixel 1008, using color density encoding, using holographic encoding, using reflective encoding, etc.

In some embodiments, each genotype pixel 1004 may represent a single genomic position and the encoding applied to each subpixel 1008 of the genotype pixel 1004 may represent a nucleotide. If a subpixel 1008 is encoded with a first value (e.g., white, black, selected color, magnetically charged, reflective, holographic, etc.), then the nucleotide is determined to be present in the patient's genotype of that particular genomic position. If a subpixel 1008 is note encoded with the first value or is encoded with a second value (e.g., black, not magnetically charged, not reflective, not holographic, etc.), then the nucleotide is determined to not be presented in the patient's genotype of that particular genomic position.

While the genotype pixel 1004 is depicted as being constructed of square subpixels 1008, it should be appreciated that embodiments of the present disclosure are not so limited. Rather, non-rectangular polygons, circles, ovals, or the like can be used as subpixels 1008 to encode intrinsic, omics, or bio-information of the author without departing from the scope of the present disclosure. For example, the pixel array could be replaced with a 90 degree arch of a circle, where each arch represent genotypes. Still further, a polygon could be used to represent genotypes. A genotype polygon have a left side and a right side where the two sides joined together represent a genotype. Consider an embodiment where A is represented by a triangle, C by a square, T by a pentagon, and G by a hexagon. The genotype AA could be represented by a full equilateral triangle, which becomes the pixel. The genotype AC could be represented by a left half an equilateral triangle joined with a right half of a square. Thus, all 10 genotypes could be represented by shapes, which could be identified via edge detection techniques (e.g., canny edges, U.S. Pat. No. 9,412,176, etc.). Such polygons can be surrounded by a border (e.g., white space, known color, transparency, etc.) to improve edge determination.

Figure 11:
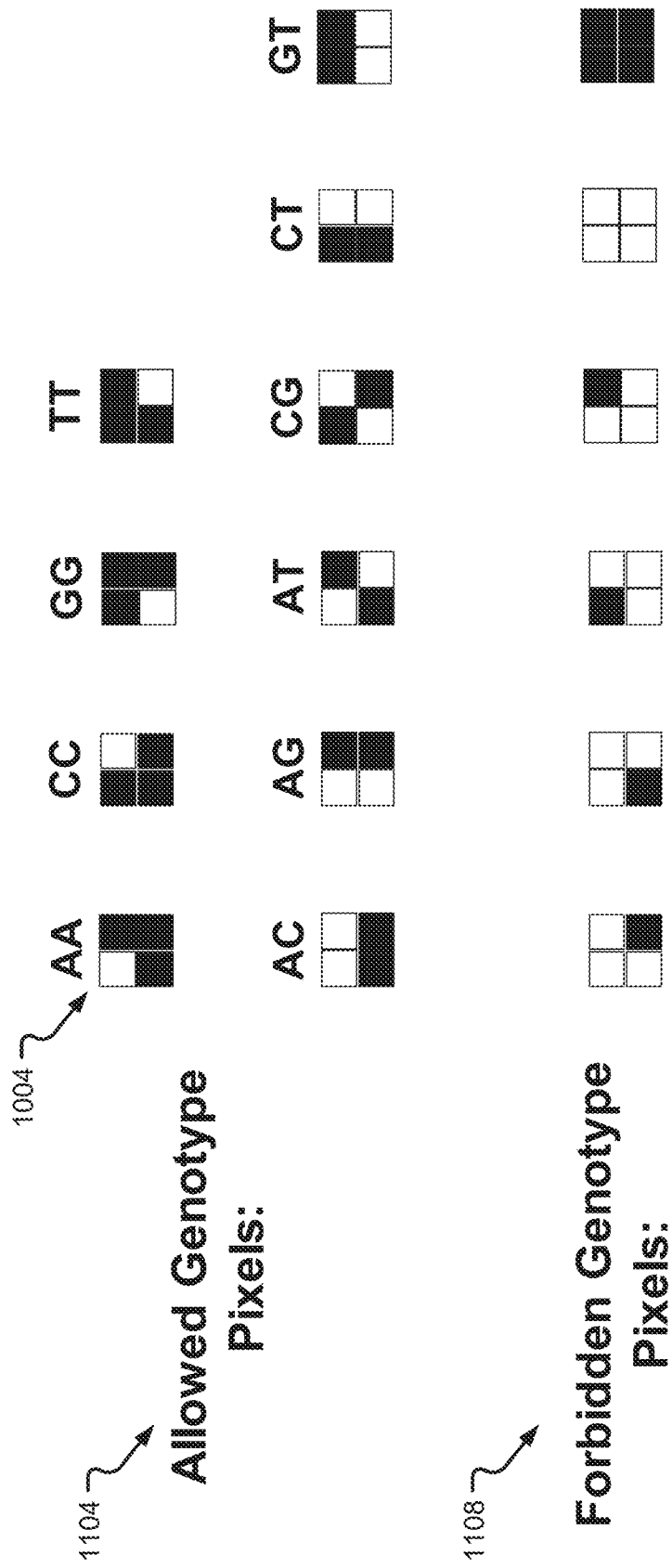
FIG. 11 illustrates allowed genotype pixels and forbidden genotype pixels in accordance with embodiments of the present disclosure.

As can be seen in FIG. 11, there may be a number of allowed genotype pixels 1104 and a number of forbidden genotype pixels 1108. Allowed genotype pixels 1104 and forbidden genotype pixels 1108 may be determined based on the possible genotypes and impossible genotypes. As a specific example, forbidden genotype pixels 1108 may include any genotype pixel 1004 that has more than three subpixels 1008 encoded with a first value (e.g., white) representing the presence of three or more nucleotides in a genomic position, which is impossible. Rather, because a single genomic position can only have nucleotide pairs (e.g., two different nucleotides or a pair of the same nucleotides), it is impossible for a genomic position to positively include three or four nucleotides. Thus, any genotype pixel 1104 representing a genomic position to have three or more nucleotides (or no nucleotides) should be considered a forbidden genotype pixel 1108. Conversely, any genotype pixel 1104 representing a genomic position to have one or two nucleotides may be considered an allowed genotype pixel 1104. Knowledge of allowed genotype pixels 1104 and forbidden genotype pixels 1108 can be used when analyzing images or pixel maps that are encoded with a unique subset of genotypes from a patient's sequenced genome.

Figure 12:
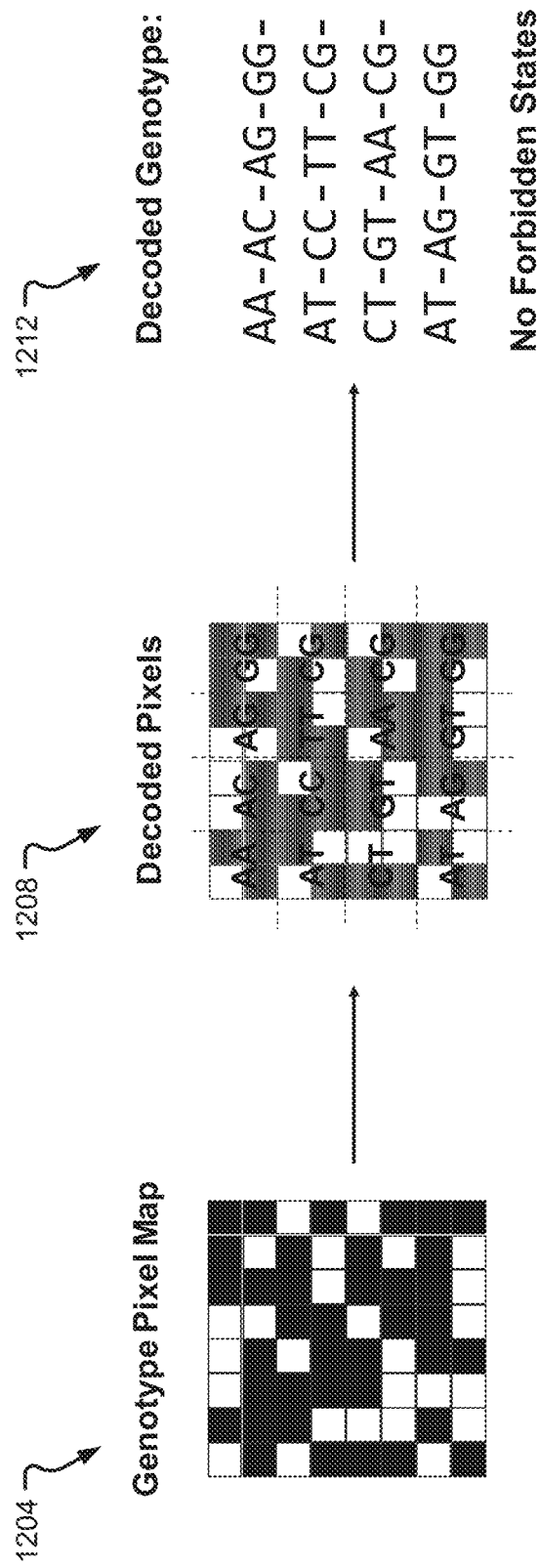
FIG. 12 illustrates an example genotype pixel map in accordance with embodiments of the present disclosure.

Referring now to FIG. 12, a first example genotype pixel map 1204 will be described in accordance with embodiments of the present disclosure. The illustrative genotype pixel map 1204 corresponds to a 16 genotype pixel map where sixteen possible positions in the genotype pixel map 1204 can each take on one of ten possible genotypes. This means that a 16 genotype pixel map 1204 can have $10^{16}$ possible combinations of values.

In the illustrative embodiment, the genotype pixel map 1204 may be decoded based on values of each subpixel 1008 in a genotype pixel 1004. Decoding the genotype pixel map 1204 based on the values of each subpixel 1008 may result in decoded pixel groups 1208, which can be further decoded to a decoded genotype 1212. In the depicted example, the genotype pixel map 1204 is determined to result in a decoded genotype 1212 that has no forbidden states. In other words, the genotype pixel map 204 is constructed entirely of allowed genotype pixels 1104 and includes no forbidden genotype pixels 1108.

Figure 13:
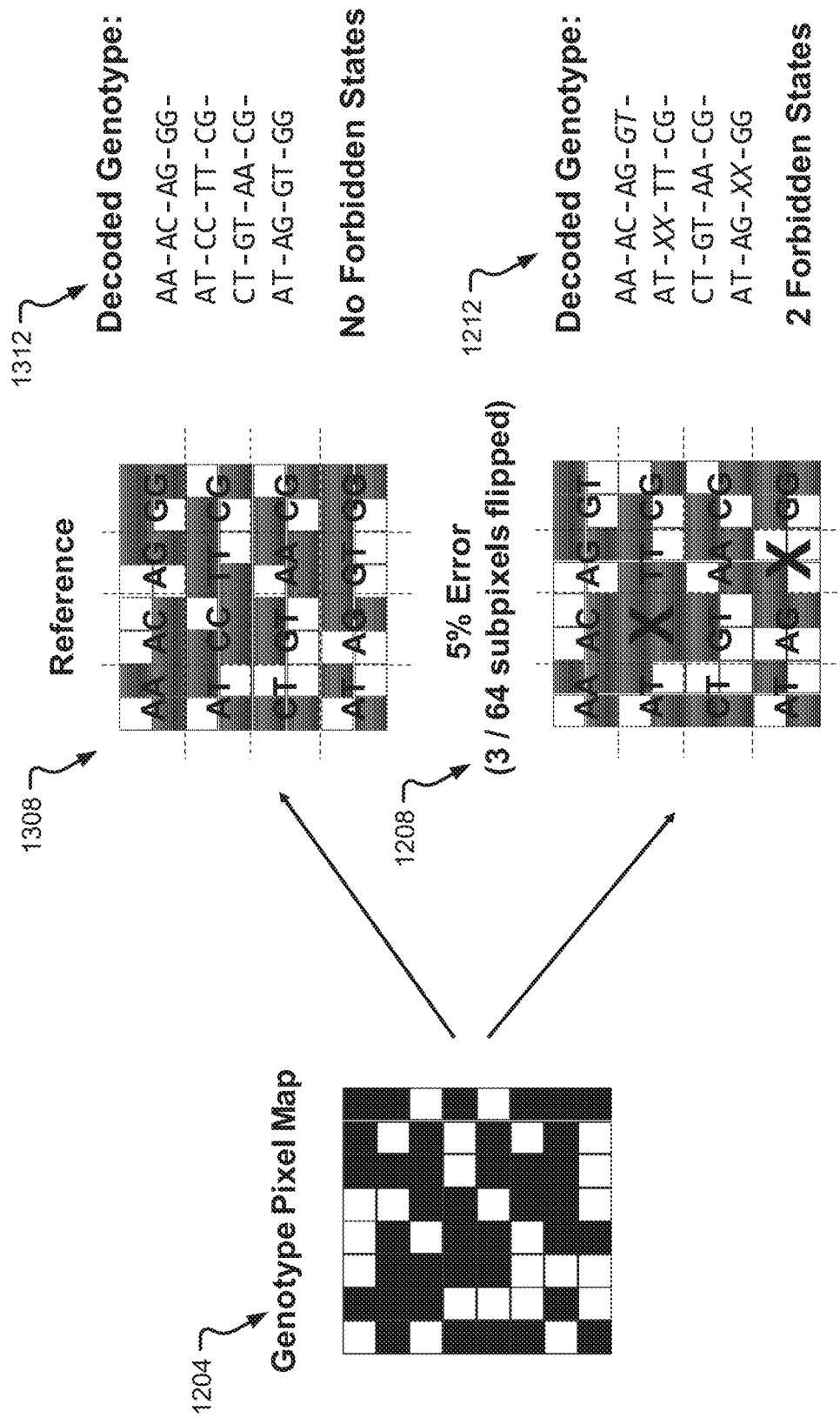
FIG. 13 illustrates a first example of read errors obtained during reading an image containing a genotype pixel map in accordance with embodiments of the present disclosure.

FIG. 13 illustrates a process for reading a genotype pixel map 1204 and continues use of the 16 genotype pixel map 1204 from FIG. 12. The process for reading the genotype pixel map 1204 may help to determine whether any read errors in connection with reading a genotype pixel map 1204. Alternatively or additionally, the process for reading the genotype pixel map 1204 may help determine whether the genotype pixel map 1204 was improperly encoded with bad genotype data, possibly indicating a data corruption problem or a possible fraudulently-generated genotype pixel map 1204. It should be appreciated that an image or published content as depicted and described herein may include a genotype pixel map 1204. The image or published content may include the genotype pixel map 1204 on just a portion thereof or the entirety of the image or published content may be presented using the genotype pixel map 1204 (which may be larger than a 16 genotype pixel map). The illustration of the 16 genotype pixel map 1204 is for ease of understanding the principles described herein.

In the illustrative example, a genotype pixel map may be read and converted to decoded pixel groups 1208, which correspond to the data actually read out of the genotype pixel map 1204 by an image capture device (e.g., a camera, a scanner, etc.). As discussed in connection with FIG. 12, the decoded pixel groups 1208 may then be converted to a decoded genotype 1212, which represents the data read out of the genotype pixel map 1204. The decoded genotype 1212 is shown to include 2 forbidden states (e.g., two forbidden genotype pixels 1108). This immediately suggests a possible read error.

FIG. 13 further depicts a reference 1308, which can be converted to a reference decoded genotype 1312. It can be seen that the decoded genotype 1212 differs from the reference decoded genotype 1312 by more than two genotype pixels 1004. In particular, two of the genotype pixels 1004 correspond to forbidden genotype pixels 1108 and another one of the genotype pixels 1004 is different from a genotype pixel 1008 of the reference decoded genotype 1312. This means that the act of reading and decoding the genotype pixel map 1204 resulted in three read errors, meaning that 3 of 64 genotype pixels 1004 were flipped. Other than the two forbidden genotype pixels 1108, only one other genotype pixel 1004 was erroneously decoded. The presence of forbidden states (e.g., forbidden genotype pixels 1108) provides a direct measure of the read error rate even though one other genotype pixel 1004 was not accurately decoded.

It may be possible to exploit locations of forbidden states in a genotype pixel map 1204 to determine the correct alignment of the pixel map in an image or published content. Said another way, it may be possible to find genotype pixel alignment in two dimensions (e.g., x and y dimensions) by shifting pixel map alignment a number of times and then determining which alignment resulted in the fewest number of forbidden states. This process will now be described with reference to FIGS. 14 and 15.

Figure 14:
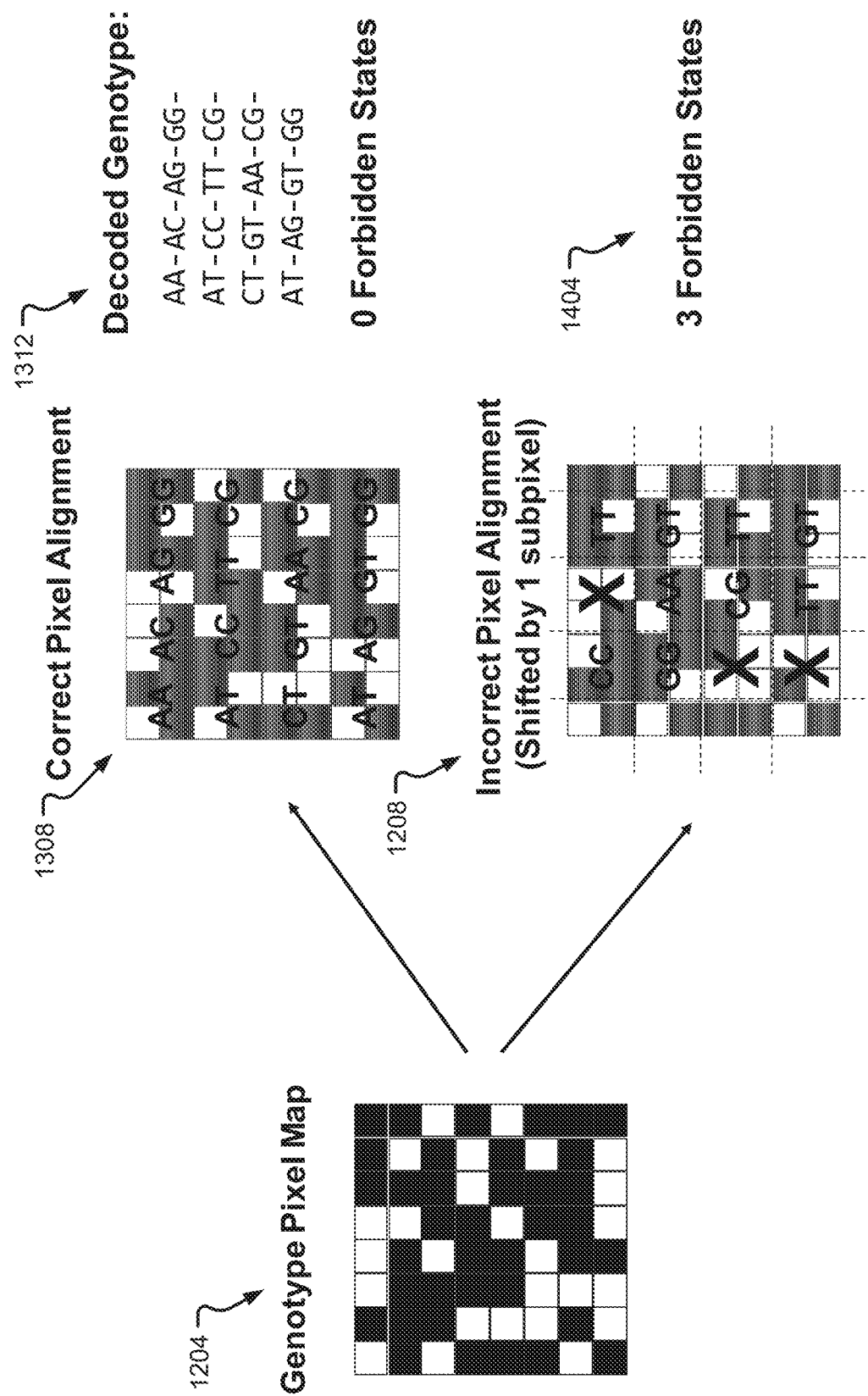
FIG. 14 illustrates a second example of read errors obtained during reading an image containing a genotype pixel map in accordance with embodiments of the present disclosure.
Figure 15:
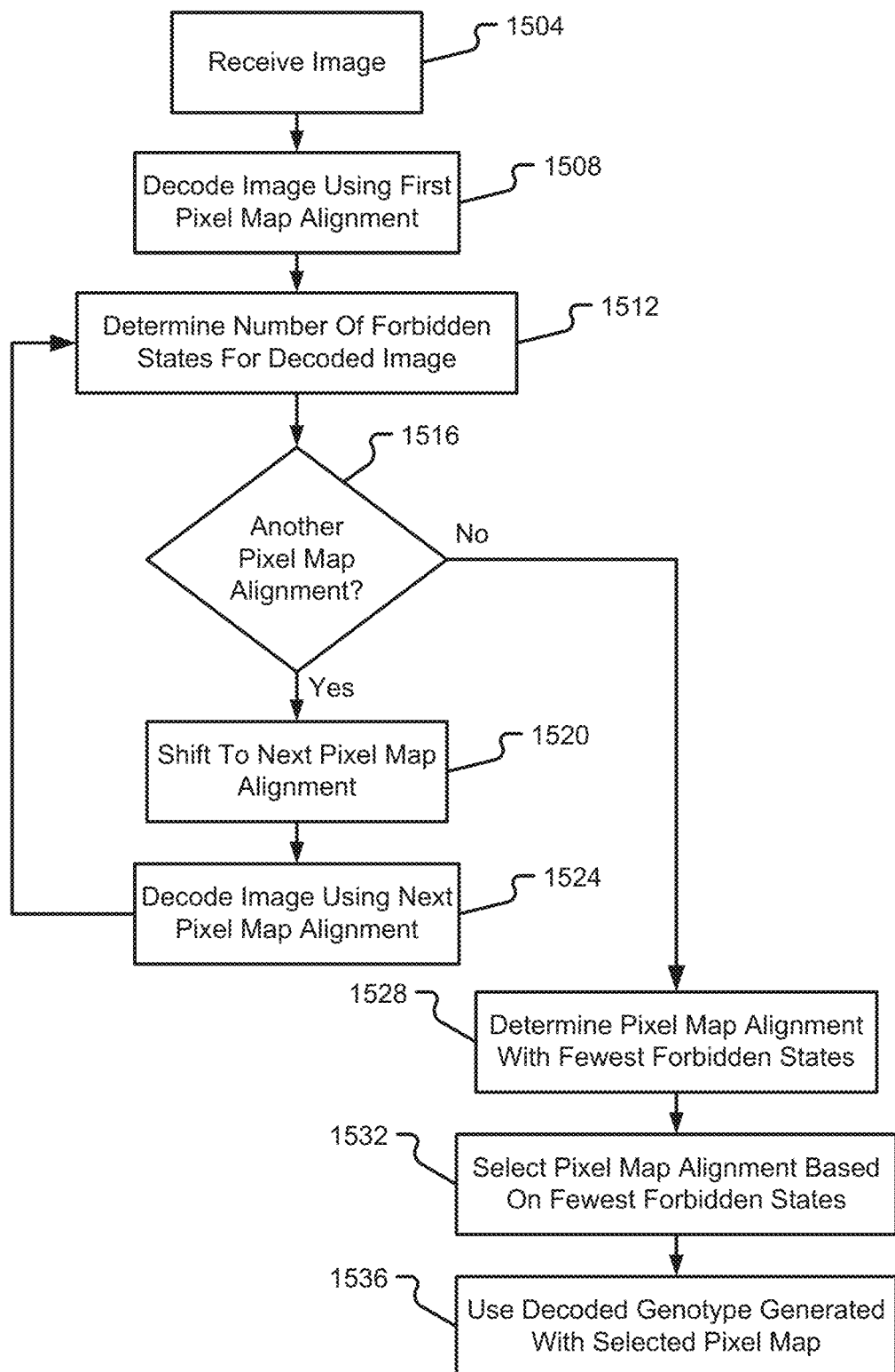
FIG. 15 is a flow chart depicting a method of processing an image in accordance with embodiments of the present disclosure.

The process begins when an image or published content is received (step 1504). In particular, an image capture device may be used to capture an image of published content, which may include, for example, an authentication token, that has been encoded in accordance with embodiments described herein. The captured image may then be decoded using a genotype pixel map 1204 and a first pixel map alignment relative to the image (step 1508). As can be seen in FIG. 14, a perfectly decoded genotype pixel map 1204 will provide perfect match with a reference decoded genotype 1312. One aspect of the present disclosure is to enable a determination of a proper pixel alignment without necessarily requiring a comparison between the decoded pixel group 1208 and the reference 1308 because such comparisons may require a large amount of processing (e.g., time and computing hardware) if the decoded pixel group 1208 contains a large number of genotype pixels 1004. Accordingly, embodiments of the present disclosure use knowledge of forbidden genotype pixels 1108 to make a first determination on whether or not a proper alignment is being used during decoding. Specifically, based on a processing of the image with the first pixel map alignment, a number of forbidden states 1404 is determined (step 1512). This information may be stored in computer memory as it will later be compared with the number of forbidden states 1404 determined for other alignments.

Thus, the method may continue by determining if there is another possible pixel alignment that can be used to decode the genotype pixel map 1204 (step 1516). In the specific example described herein, there may be four possible alignment that can be used to decode the genotype pixel map 1204. The specific alignments may include a first alignment, a second alignment that is offset from the first alignment by one subpixel column, a third alignment that is offset from the first alignment by one subpixel row, and a fourth alignment that is offset from the first alignment by a combination of one subpixel row and one subpixel column. If the genotype pixels 1004 were organized differently (e.g., in a 4×1 array or 1×4 array), then the possible alignments would vary only by shifting 1, 2, or 3 columns or by shifting 1, 2, or 3 rows.

In any event, if less than all of the possible alignments have been used to decode the genotype pixel map 1204, the method may continue by shifting to a next possible pixel map alignment (step 1520). Using the new alignment, the image may again be decoded (step 1524) and the number of forbidden states 1404 may be determined for new alignment (step 1512). This process will repeat until all possible alignments have been explored and a number of forbidden states 1404 is determined for each possible alignment. Eventually, after all possible alignments have been explored, the query of step 1516 will be answered negatively and the method will continue by determining which pixel map alignment resulted in a fewest number of forbidden states 1404. The pixel map alignment that achieved the fewest number of forbidden states 1404 will be selected (step 1532). The decoded pixel group 1208 from the selected pixel map alignment may then be used for further image processing (step 1536). For example, the decoded pixel group 1208 from the selected pixel map alignment may be used for image validation. Alternatively, the selected pixel map alignment may be applied to an image to decode individual pixels or to extract information from the image.

Figure 16:
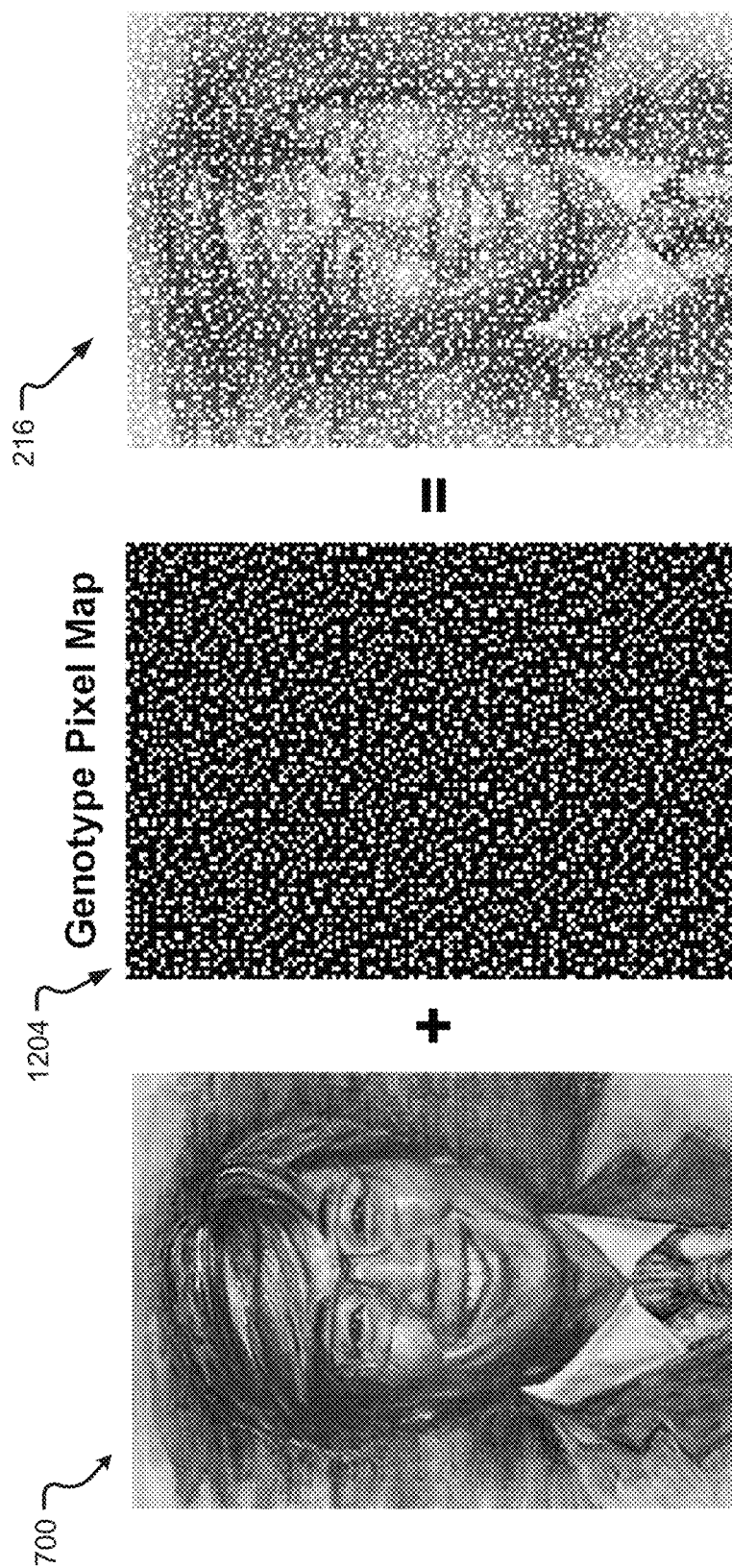
FIG. 16 illustrates an example of scaling pixel maps in accordance with embodiments of the present disclosure.

With reference now to FIG. 16, an illustrative example of authentication tokens 216 generated with genotype pixel maps 1204 will now be described in accordance with at least some embodiments of the present disclosure. Specifically, FIG. 16. illustrates how an image 700 can be converted into an authentication token 216 by use of a genotype pixel map 1204. As discussed above, a genotype pixel map may include any number of author-specific genotypes and may be represented with a corresponding number of genotype pixels 1004. Further, the author-specific genotypes can also be altered as discussed above with respect to virtual sequences. The genotype pixel map 1204 of FIG. 16 is shown to include more than 3,700 patient-specific genotypes composed of: (1) approximately 2,000 "common" SNPs (e.g., SNPs present in more than 5% of the global population); (2) approximately 250 population-specific SNPs; and (3) approximately 250 chromosome X SNPs (e.g., heterozygous only in females). If the authentication token 216 generated with this particular genotype pixel map 1204 were printed on a credit card or other identification document (e.g., driver's license, passport, etc.), the authentication token 216 would require approximately 2 inches×2 inches of space for reproduction. Such an image would require a resolution of approximately 50 PPI (pixels per inch).

If such a resolution is not possible, then it may be necessary to decrease the number of genotype pixels 1004 in the genotype pixel map 1204, increase the size of the space used to print/present the authentication token 216, or a combination thereof. Otherwise, the printing/reproduction limits will result in an authentication token 216 that cannot be accurately produced and/or read. When used in connection with an identification document, this limitation can be overcome by employing a suitable genotype pixel map 1204 or reproduction process.

Figure 17:
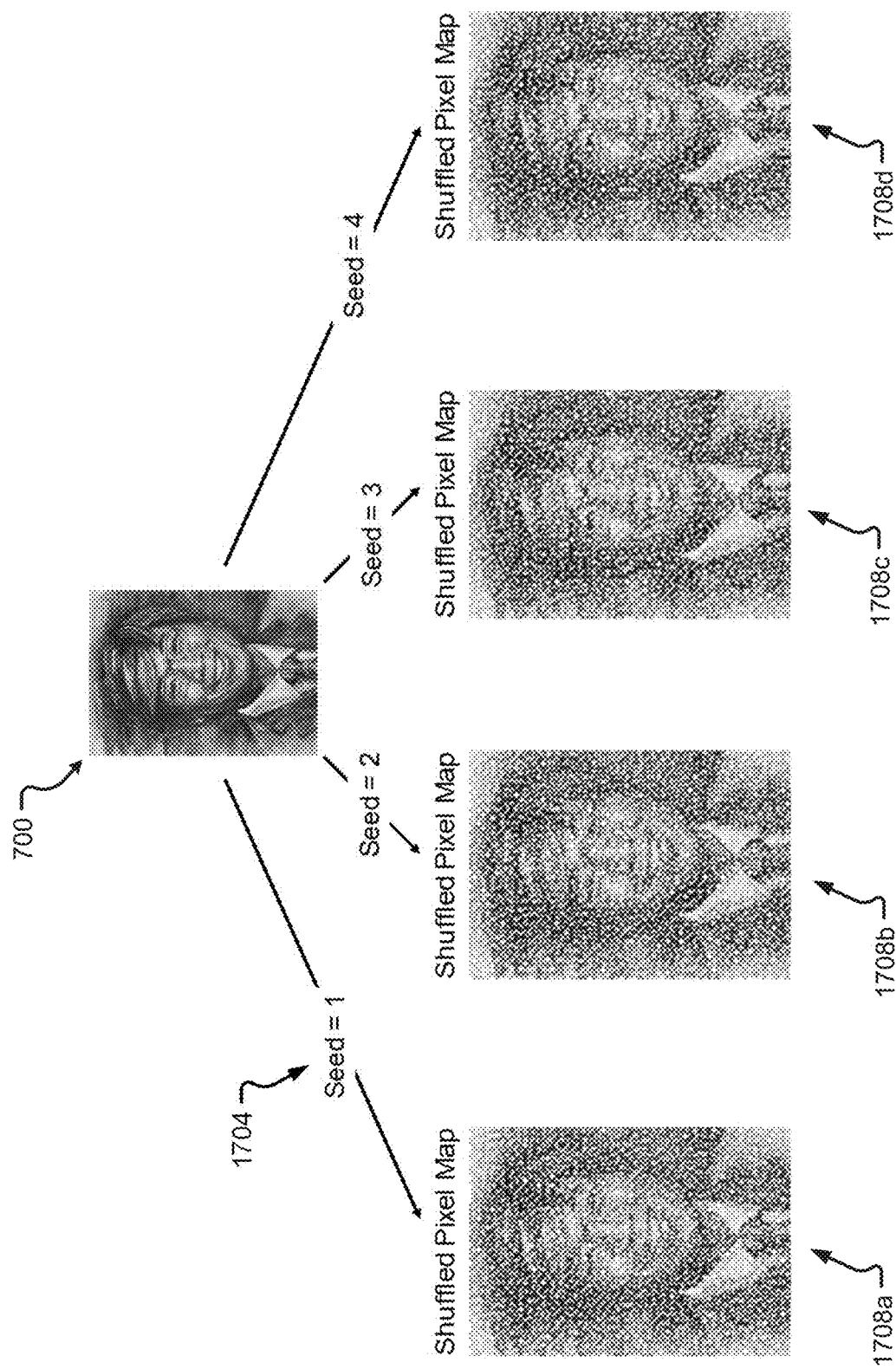
FIG. 17 illustrates a process for generating one or multiple shuffled pixel maps in accordance with embodiments of the present disclosure.

When using an authentication token 216 in an identification document, it may be desirable to obfuscate at least some personal data prior to printing a reproduction of the authentication token 216; otherwise, analysis of the authentication token 216 may result in a divulgence of personal information (e.g., genomic information). One possible approach to obfuscate or hide personal information is to utilize a deterministic function to produce the genotype pixel map 1204. FIG. 17 illustrates one example of using a seed value 1704 to generate multiple different (e.g., unique) pixel maps 1708a, 1708b, 1708c, 1708d, where the number of pixel maps generated can vary from 1-N, with N being any integer value greater than or equal to two.

In the depicted embodiment, each seed 1704 used to generate a different pixel map 1708a, 1708b, 1708c, 1708d can correspond to a randomly generated numeric value. It is likely difficult to tell in the published figures of this document, but each of 1708a through 1708d do indeed have different pixelated patterns while maintaining the image integrity of the authentication token. The randomly generated numeric value may correspond to an output of a digital hash of a file name, of a digital hash of an original work, a time stamp, of a password, of a username, or other factors. Each pixel map 1708 may be generated with a shuffled version of a reference genotype pixel map 1204. Specifically, a reference genotype pixel map 1204 may be obtained based on a patient's actual genomic information, but then a shuffled pixel map may be determined by applying a randomly determined seed value as an input to a deterministic function, then the shuffled pixel map may be used in place of the reference genotype pixel map 1204 to transform an image 700 into a different pixel map 1708. In the example of FIG. 17, the different pixel maps 1708a, 1708b, 1708c, 1708d may correspond to possible versions of an authentication token 216 to be used on an identification document or in connection with one or more published content or original works as described herein. The shuffled pixel map and/or different pixel map 1708 generated with the shuffled pixel map may be stored in memory 116 of the digital media management server 108. Thus, even if a bad actor gains access to the digital media management server 108, the bad actor will not have access to the patient's personal genomic information. Rather, they will only be able to access the shuffled pixel map and/or different pixel map 1708. Furthermore, when a one-way deterministic function is used, it may be impossible for a bad actor to reverse engineer a patient's genotype. It should be appreciated that more than one pixel map 1708a, 1708b, 1708c, 1708d may be generated for different uses and/or for different servers/publishers.

Figure 18:
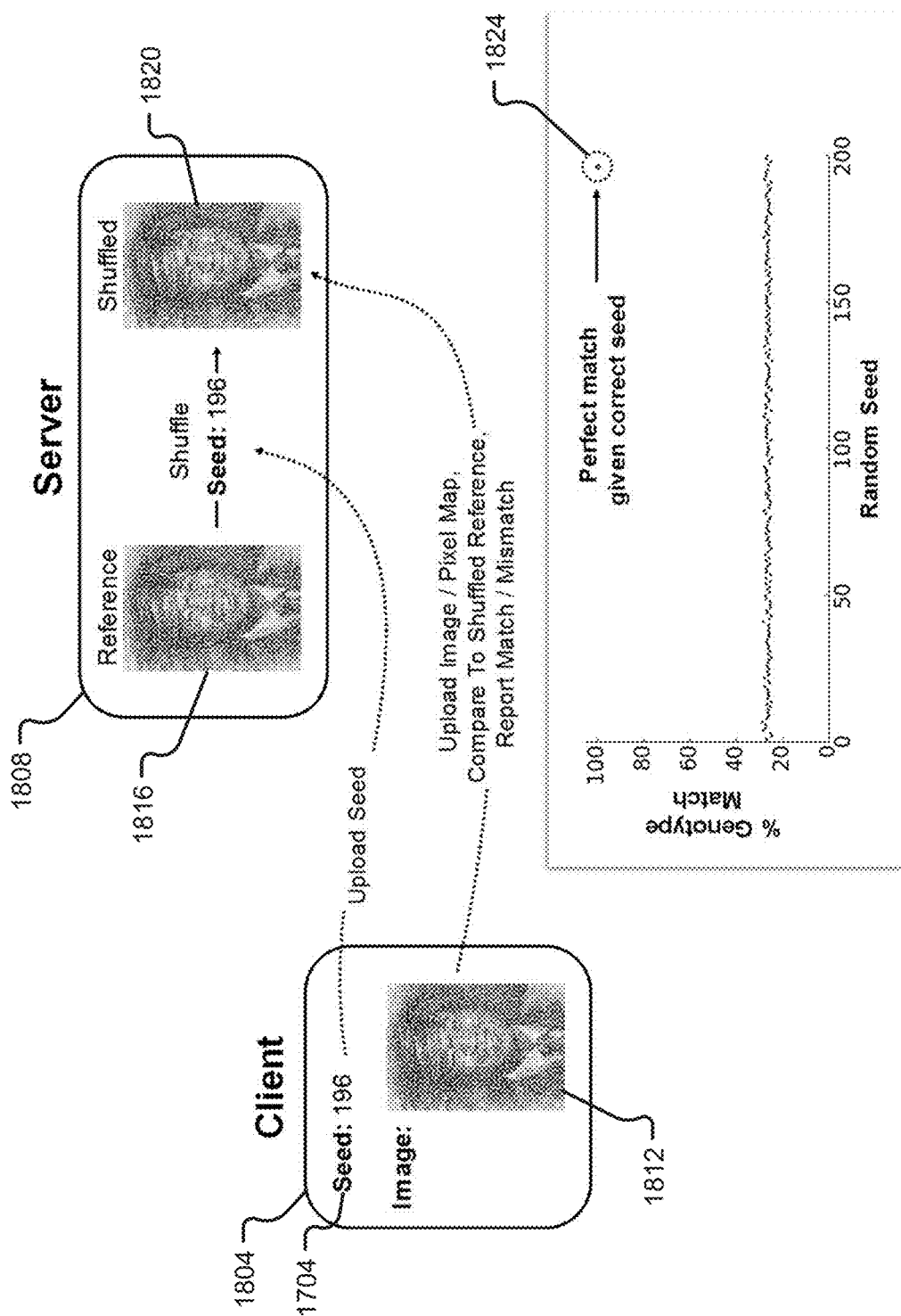
FIG. 18 illustrates an identity validation process in accordance with embodiments of the present disclosure.
Figure 19:
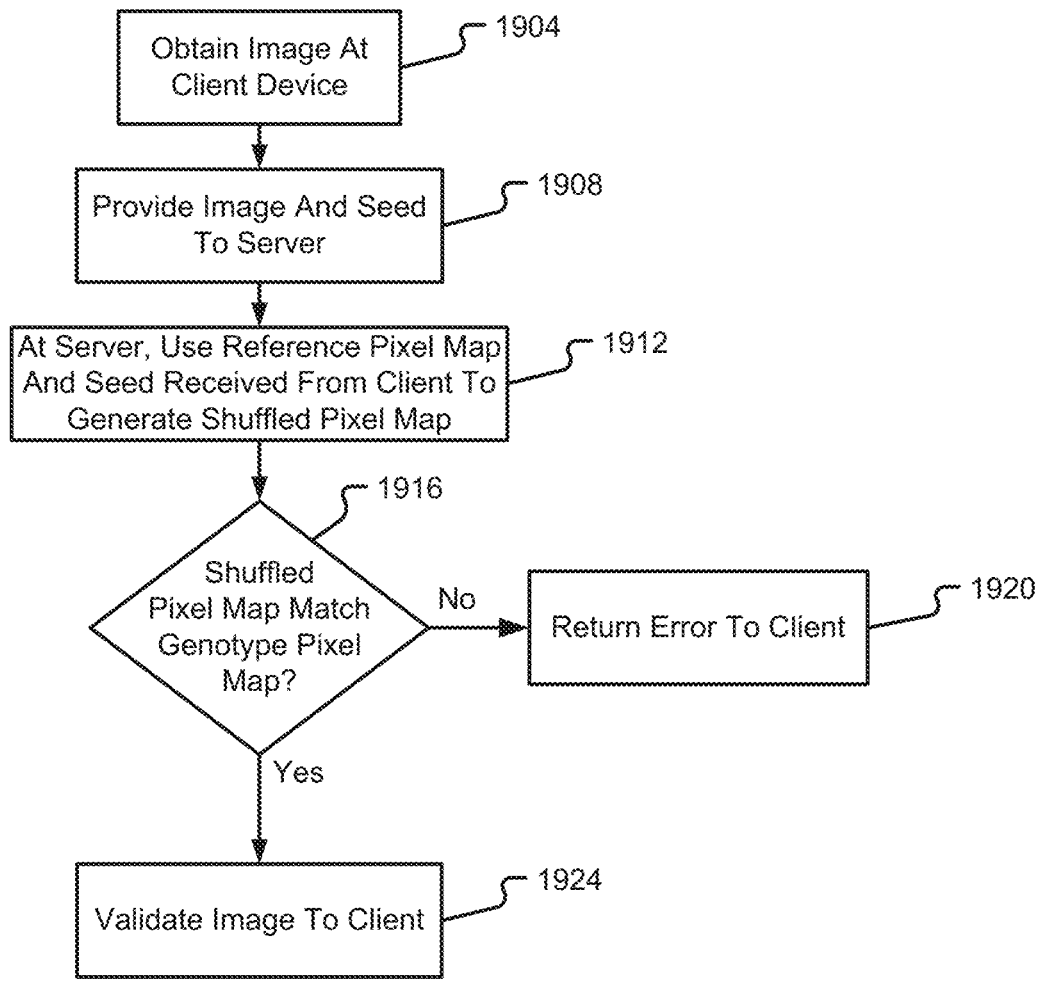
FIG. 19 is a flow chart depicting a method of performing the identity validation process depicted in FIG. 18.

With reference now to FIGS. 18 and 19, additional details regarding identity or image validation will be described in accordance with at least some embodiments of the present disclosure. The method begins by obtaining an image 1812 at a client device 1804 (step 1904). The image may correspond to an image captured by an image capture device of the client device 1804 (e.g., a camera embedded in the client device). Alternatively or additionally, the image include information obtained from a computer-readable storage medium (e.g., computer memory). The image 1812, in such an embodiment, may correspond to image data that has been encoded for transmission via means other than image capture (e.g., Bluetooth, NFC, etc.).

The method may continue with the client 1804 providing the image 1812 (or data describing the image 1812) to a server 1808 along with a seed value 1704. The seed value 1704 may correspond to a value obtained from a publisher of the image 1812 (e.g., a publisher of the published content). Alternatively or additionally, the seed value 1704 may be provided as part of a URL that directs a browser of the client 1804 to a website hosted by the server 1808. The seed value 1704 may correspond to a seed value used to generate the image 1812 as displayed with the published content.

The method may continue with the server 1808 using its reference pixel map 1816 and the seed value received from the client 1804 to generate a shuffled pixel map 1820 (step 1912). The shuffled pixel map 1820 may be compared to the image 1812 to determine if there is a substantial match between the two (step 1916). If there is not a substantial match (e.g., the two pixel maps do not match within a predetermined threshold amount, say at least 95% of pixels from one image match pixels from the others), then the server 1808 may return an error message to the client 1804 (step 1920). The error message may indicate that the server 1808 failed to achieve a match and/or that the image 1812 received from the client 1804 is invalid. On the other hand, if there is a substantial match, then the server 1808 may determine that the image 1812 is valid and provide the client 1804 with a message indicating the same (step 1924). At this point, the client 1804 may perform additional steps consistent with determining that the image 1812 is valid (e.g., opening another webpage, downloading content from a server other than server 1808, downloading content from server 1808, etc.).

Figure 20:
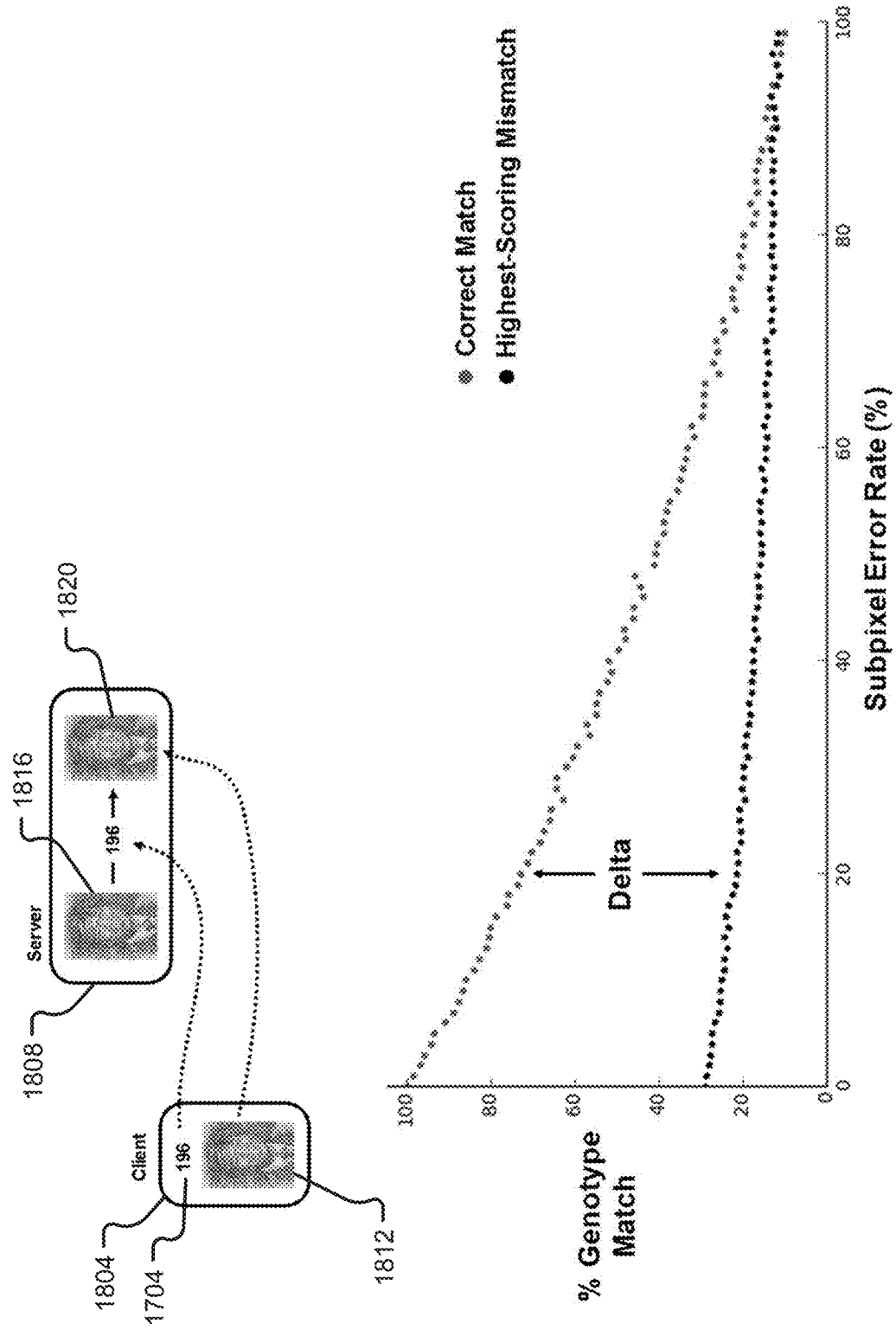
FIG. 20 illustrates an identity validation and imaging error detection process in accordance with embodiments of the present disclosure.
Figure 21:
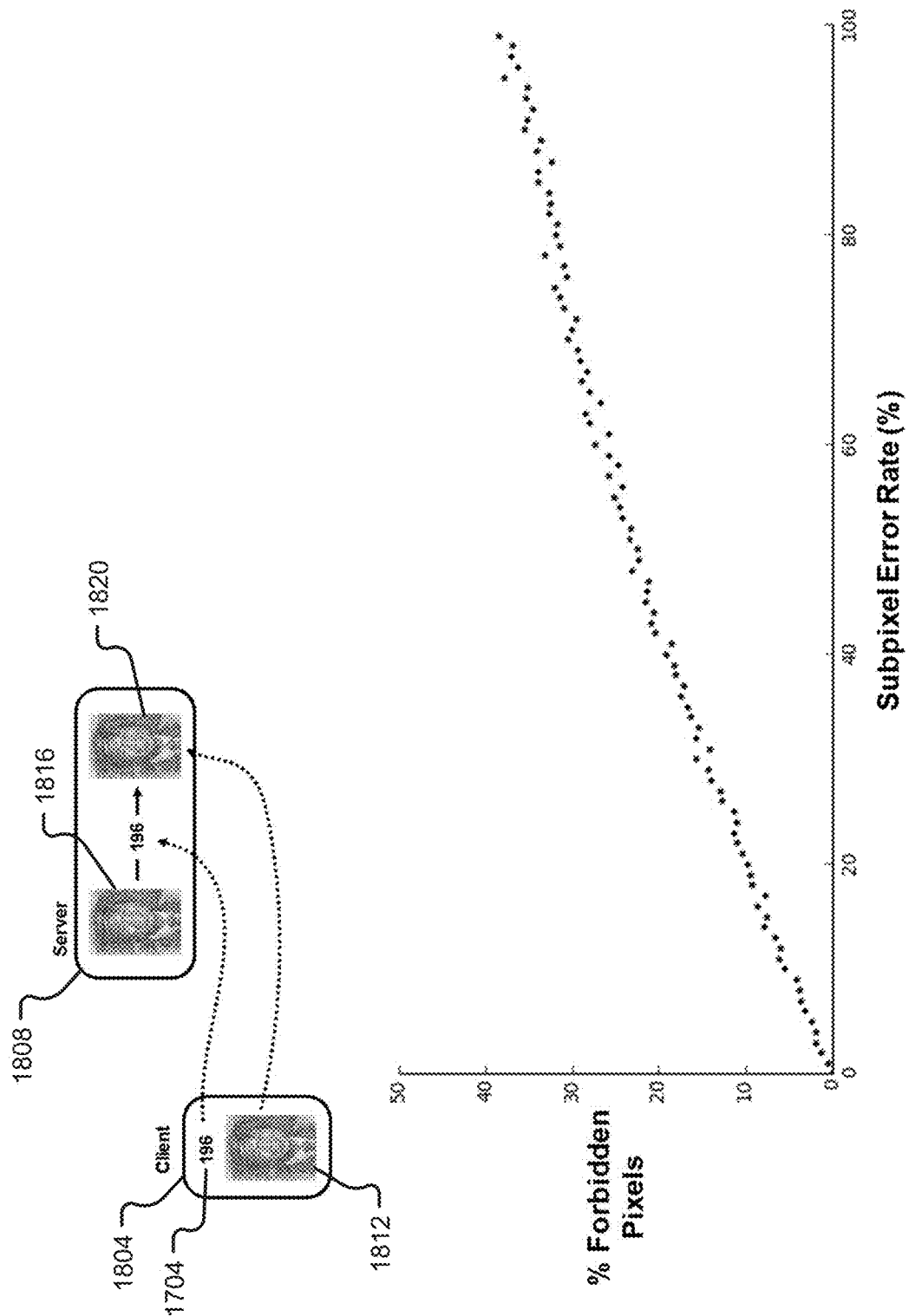
FIG. 21 illustrates another identity validation and imaging error detection process in accordance with embodiments of the present disclosure.
Figure 22:
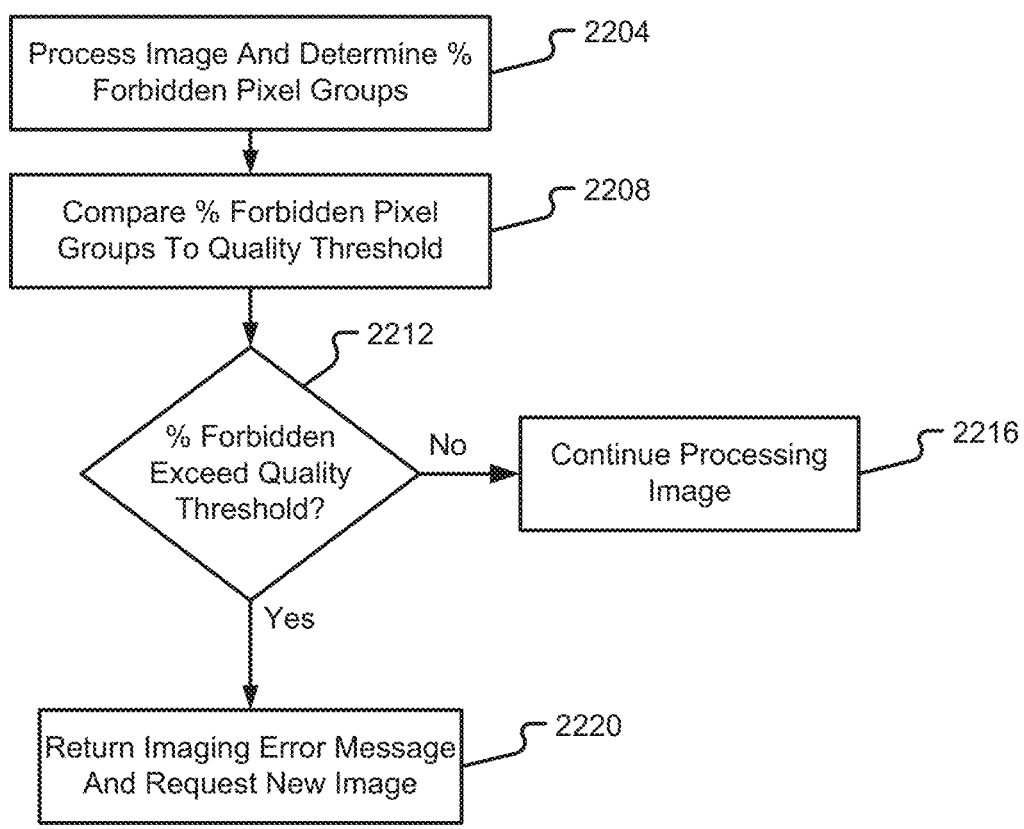
FIG. 22 is a flow chart depicting a method of performing identity validation and imaging error detection in accordance with embodiments of the present disclosure.

With reference now to FIGS. 20-22, additional details regarding identity validation and imaging error detection will be described in accordance with at least some embodiments of the present disclosure. The scenarios described with reference to FIGS. 20 and 21 may be similar to that of FIG. 18, except that the client 1804 may introduce some errors when resolving subpixels 1008 of the image 1812. Again, the client 1808 may obtain an image 1812 (e.g., by capturing an image of an authentication token 216 or of published content) with an image capture device of the client 1804.

The captured image 1812 and a seed value 1704 may be provided to the server 1808 for analysis and identity validation. In the example of FIG. 20, it can be seen that if delta is greater than zero, then a correct match is found and the image 1812 can be validated. Specifically, a correct match can be identified even when the image reader of the client 1804 makes errors in more than 90% of the subpixels 1008. In the example of FIG. 21, it can be seen that as subpixel 1008 error rates increase, so too does the observance of forbidden pixels 1108. Thus, the server 1808 may be able to quickly determine if the quality of the image 1812 is insufficient when the number of forbidden pixels 1108 exceeds a predetermined threshold (e.g., 25%). It should also be appreciated that the client 1804 may perform this process of analyzing forbidden pixels 1108 before sending the image 1812 to the server 1808, thereby preserving network resources unless/until the client 1804 determines that the quality of the image 1812 is sufficient for further analysis and processing by the server 1808. Said another way, if the client 1804 determines that the captured image 1812 includes more than a predetermined number (or percentage) of forbidden pixels 1108, then the client 1804 may instruct a user of the client 1804 to capture another image 1812.

As shown in FIG. 22, either the client 1804 or server 1808 (or both) may perform an image processing method to determine image quality prior to committing further processing resources to decoding the image. The method begins when the client 1804 or sever 1808 process the image 1812 and determine a number (or percentage) of forbidden pixels 1108 in the image 1812 (step 2204). The number (or percentage) may then be compared to a predetermined quality threshold (step 2208) to determine if the number (or percentage) exceeds the predetermined quality threshold (step 2212).

If the query of step 2212 is answered negatively, then the image 1812 may be further processed (step 2216). In some embodiments, further processing may include transmitting the image 1812 from the client 1804 to the server 1808. In some embodiments, further processing may include decoding the genotype pixels 1004 of the image 1812, comparing the image 1812 to another shuffled pixel map 1820, etc. If the query of step 2212 is answered positively, then the method may include returning an imaging error message to a user of the client 1804 (step 2220). The imaging error message may include instructions or a request for a new image.

The various embodiments and techniques provided herein relate to the use of a token for purposes of identifying a person. While certain examples were used to identify a person as an artist or content creator, it should be appreciated that the claims and embodiments described herein are not so limited. Rather, a token or authentication token as described herein may correspond to a universal human identifier, universal patient identifier, or the like. That is to say, the term "human" should not be construed as limiting embodiments provided herein. In the context of the creation of art, the universal human identifier could be considered a universal artist identifier. It should be appreciated, however, that other contexts may provide different use cases for the tokens described herein.

The techniques and technologies provided herein give rise to many interesting use cases. In some embodiments, the digital work tokens can vary with time. Consider a scenario where an author is working on a long term project, say a portrait or a sculpture. At each stage of the project, a new digital work token can be generated to notarize the work in progress. The state of the work can be captured (e.g., image, 3D scan, audio file, etc.) and converted to a work hash, which is then used to create a new digital work token. Further the digital work token could also be based on the previous stage's digital work token in a similar fashion as blocks in a blockchain depend on the hash value of a previous block. Each stage of the work, the digital work token for each stage, and so on can be chronicled on a blockchain or other distributed ledger technology. From the perspective of a video digital work, as a person watches the video, the digital work token could also vary with time. The image itself could vary while the embedded DNA remains the same, the virtual DNA sequence could vary in time while the image remains the same, or both could vary with time.

In similar vein to tracking stages of a long term project, the disclosed techniques can also be applied to healthcare. For example, a patient undergoing a long term personalized treatment might be best served by such tokens from multiple perspectives. First, a token can be generated that is paired with treatment at a point of care. A doctor can validate the token before providing the corresponding treatment to ensure that the patient is indeed receiving the correct treatment. Second, the doctor could also have a token representing his work and the stage of the treatment so the patient has a high degree of certainty (upon validation) that they are receiving the proper treatment by the correct, authorized individual. Third, the patient's health can be tracked and notarized by updating the patient's token by treating the patient's vital signs or other health state as a "work" that is then integrated into the patient's token.

Although the disclosed techniques are discussed with respect to digital works such as images or text-based articles, it should be appreciated that the techniques can be applied to other modalities. Digital audio works are quite amenable to the disclosed techniques due to the ease of processing a digital audio file. More esoteric modalities are also contemplated including real-world 3D sculptures, augmented reality or virtual reality rendering (e.g., 2D, 3D, etc.), mechanical works (e.g., engines, motors, automobiles, aircraft, etc.), construction, buildings, inspections, dance, software code files, or other types of modalities. For these more esoteric modalities, the work can be digitized through one or more techniques possibly including capturing video images of the work, laser scanning the work (e.g., 3D scan), capturing X-rays of the work or object, or via other digitizing techniques.

Thus far, the digital work token has been described as being based on an image or portrait of an author. It is also contemplated that the token could be based on any desired image or digital rendering, perhaps an image of a favorite pet for example. Still further the digital token could leverage more than one image rather than a single image where the two or more members of the digital token set would be required for validation purposes, say three tokens in a set of five are required to validate the work. This can be achieved via having overlapping features among the tokens in the set. For example, each token could have a partial valid token DNA sequence and a false DNA sequence such that three tokens of the five are needed to create a complete set. The complete valid DNA sequence can be broken down into five parts. The first token might have parts 5, 1, and 2; the second token would have 1, 2, and 3; the third token would have 2, 3, and 4; the fourth token would have 3, 4, and 5; and the fifth token would have 4, 5, and 1. Thus, any three tokens would necessarily provide a complete valid DNA sequence for validation purposes.

An interesting application of the disclosed technique includes using the disclosed digital authentication tokens to mitigate the risk of fake news. There are multiple facets to such an application. Consider the LA Times® newspaper. When a reporter or journalist writes a news article, a corresponding digital work token can be generated and presented along with the article. Naturally, in a print format the font size and/or fidelity of the token can be adjusted to be amenable for print. In a digital form, there are less constraints or restrictions on the token. The token-article pair can be validated at any time. If a portion of the article is lifted and presented out of context along with the token, then a validation exercise would fail indicating that the article is out of context. While it is true that a person could completely fabricate a fake news story and create a corresponding token; however, they would likely lack credentials or credibility. To mitigate such nefarious activities, in some embodiments, the token can further include an embedded link (e.g., URI, URL, DOI, HOI, etc.) that points to the original source of the article, preferably a credible source such as the LA Times. This can be achieved by an encoding scheme that translates intentional sequence differences (rather than pseudo-random deterministic differences) into a URL or via a lookup database on the validation or verification servers. Just as three letters of DNA form a codon (i.e., 64 possible three letter combinations that map to amino acids), three letters of DNA in the virtual sequence could be mapped to 64 alphanumeric characters forming a URL. This approach is considered advantageous because is provided an infrastructure by which social media sites (e.g., Facebook, Instagram, Twitter, etc.) can ensure that posts are credible or verifiable.

Embodiments described herein can be leveraged to produce a movie, "Live" Photo, GIFs pixel maps, and/or lenticular prints. This may be achieved by encoding more genotypes using a time dimension, where each frame uses another set of genotypes. Frames could be configured to loop, with key frames (e.g., as denoted by a certain pixel map pattern) to mark the beginning of the loop. Using this technique, it could be possible to encode a full exome (38 million genotypes) in a ~7 min movie using 60×60 pixel maps (3,600 genotypes): 38,000,000 genotypes/3,600 genotypes/second=10,555 frames==>439 seconds (7m20s)@24 frames/second. As another example, lenticular prints could encode two pixels maps (e.g., as viewed from left vs. right) to double the amount of genotype data.

Another aspect of the present disclosure may be to disallow certain random hashes at the server level. Consider the scenario where person A generates tokens with hashes 1, 2, 3, 4 and gives them out to their family/coworkers/etc. If token #2 is lost or stolen, then person A may request that hash #2 be disallowed on the server. In this way, anyone who finds Token #2 (and knew the correct hash) would not be able to use it. This concept could also be used to create "temporary" or one-time-use tokens by disallowing their random hashes after a certain duration and/or number of times used.

Another aspect of the present disclosure is to utilize a rotating "reference" token stored on a hash. This may be used when all identity or tokens become "compromised." If such a situation is detected, then the server-side reference token could be shuffled with a new random hash. All "old" tokens could be voided since their shuffled pixel maps will only match the "old" reference. Any comparison of "old" tokens to the newly-shuffled reference token would then result in a failed authentication. This may mean that new tokens will be generated from the server. In high security applications, it may be possible to force a reference shuffle once every day, month, year, etc. It may also be possible to randomize the hash based on multiple inputs (e.g., hash of password+DOB+SSN, etc.). Further still, it may be possible to add a date to preset the random hash (e.g., password+DOB) so any particular hash only works on a certain date (e.g., now or in some determined future time).

Another aspect of the present disclosure may provide a secure pixel map as "stickers" to be stuck on objects. Such "stickers" may be used to prove the object's provenance, verify ownership, and/or verify a chain of custody.

Embodiments of the present disclosure may also be leveraged to produce "third party" tokens. In this situation, person A's genotype may be shuffled with person B's random hash. Person B is then allowed access to person A's health data. Person A can still "turn off" person B's access to their health data by disallowing person B's random hash or via shuffling of person A's reference genotype. The use of "third party" tokens may provide particularly useful when person A is elderly or incapacitated and person B needs access to health records, wills, etc. of person A. It may also be possible to give person A's doctor the ability to open person A's health vault to read and/or update health data for person A.

Embodiments of the present disclosure may also leverage the token to open a Genomic-Vault and trigger action(s) in the cloud. As one example, a single token may be used to generate a report at branded Kiosks (e.g., a branded kiosk at a particular store may scan a user's token and present a PGx report, which is sent to the user's doctor, pharmacist, and/or the user. In another example, a single token may be used to authorize a release of genomic data to a clinical trial/research study/ancestry pool. In another example, a single token may be used to find relatives near a particular user (who have released their data to an ancestry pool). In another example, two tokens (e.g., male & female tokens) may be used to trigger an action. The two tokens may be used start an analysis that scans each person's genomes for disease risk markers that could affect their future children. Results of the analysis could be stored in health vault of both people, linked by their tokens. In another example, two or more tokens could be used to determine a relatedness of each token to all other tokens.

In some embodiments, key markers may be encoded in a token to be acted upon at the client side. In an illustrative method: (1) server sends back pixel locations of "key markers" in shuffled pixel map; (2) client processes the data stored at those locations, then performs a specified action based on result; (3) No need to send result of client-side analysis back to server.

It should be appreciated that key markers might include any/all of the following: male/female markers; ancestry markers; pharmacogenomic markers linked to toxicity/efficacy of a specific drug; cancer/disease risk markers; etc. User-specific or group-specific key markers could also be used. For instance, if a doctor believes a patient to be at elevated risk of cardio-related illnesses, then the doctor may request cardiotoxicity markers be added to that patient's token. The server could then retain the cardiotoxicity markers as part of the patient's token.

Unique client actions could also be facilitated. Illustrative client actions could include any number of the following: discounts/promotions for people with a given ancestry (e.g., St Patty's Day for people of Irish ancestry); adjust drug dosage and/or avoid certain drugs based on PGx markers (e.g. Doc/pharmacist scans token); low level security by way of performing identity verification. As an example, the token may be used to validate whether the holder of the token exhibits certain characteristics (e.g., is holder of token=Asian Female?).

It may also be possible to provide customizable user- or group-specific key markers. In this situation, the meaning of a customized key marker may only be known to the user or the group and may be unknown by the server or any other entity.

It should be appreciated that any combination of processes depicted and described herein can be performed without departing from the scope of the present disclosure. Alternatively or additionally, any number of other authentication or verification processes can be developed by combining various portions or sub-steps of the described authentication processes without departing from the scope of the present disclosure.

Specific details were given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

What is claimed is:

1. A computer-assisted method of mitigating risk of digitally distributed fake news, the method comprising:
   storing, via at least one processor, an original digital work associated with an original news story in a non-transitory computer readable memory;
   generating, via the at least one processor, a digital authentication token through execution of an implementation of at least one deterministic function on at least a portion of the original digital work and on digital identifying information associated with a publisher of the original news story and the original digital work;
   publishing, via the at least one processor, the original digital work and the digital authentication token as a token/work pair, wherein the digital authentication token comprises an embedded link that points to the publisher of the original news story; and
   enabling, via the at least one processor, validation processing that includes generating a validation score representing a validation of a suspect news story based on deterministic features derived from the digital authentication token and from at least a portion of the suspect news story, wherein the at least one deterministic function performs at least one of a pixel-to-pixel comparison, a descriptor comparison, and an optical character recognition comparison with the at least a portion of the original digital work, and wherein the deterministic features comprise a combination of outputs from at least two of the pixel-to-pixel comparison, the descriptor comparison, and the optical character recognition comparison.

2. The method of claim 1, further comprising recording publication of the token/work pair on a notarized ledger.

3. The method of claim 2, wherein the notarized ledger comprises a distributed ledger.

4. The method of claim 3, wherein the distributed ledger comprises at least one of the following: an Openchain ledger, a Hyperledger, an Ethereum ledger, a bitcoin ledger, a TRON ledger, an IOTA ledger, a smart contract ledger, and a hashgraph ledger.

5. The method of claim 1, wherein the at least the portion of the suspect news story relates to the original digital work and wherein the embedded link is generated using an encoding scheme that translates sequence differences into the embedded link.

6. The method of claim 5, wherein the at least the portion of the suspect news story comprises a portion of the original digital work.

7. The method of claim 6, wherein the at least the portion of the suspect news story comprises an out of context presentation of the original digital work.

8. The method of claim 1, wherein the at least the portion of the suspect news story lacks a credible portion of the original digital work.

9. The method of claim 1, wherein the at least the portion of the suspect news story comprises a fake.

10. The method of claim 1, wherein the validation score indicates the at least the portion of the suspect news story is considered valid based on the token/work pair.

11. The method of claim 1, wherein the validation scores causes return of a message indicating the at least the portion of the suspect news story is invalid.

12. The method of claim 1, wherein the publisher comprises a credentialed publisher.

13. The method of claim 1, wherein the deterministic function includes at least one of the following: a hash function, a random number generator, and a recognition algorithm.

14. The method of claim 1, wherein the embedded link comprises at least one of the following: a URI, a URL, a DOI, and a HOI.

15. The method of claim 1, wherein the embedded link comprises an intentional encoding within the authentication token.

16. The method of claim 1, wherein the digital identifying information associated with the publisher identifies at least one of the following types of publishers: a newspaper, an author, an artist, a reporter, a journalist, a corporation, and an editor.

17. The method of claim 1, wherein the original digital work is a digital representation of a physical work.

18. The method of claim 17, wherein the physical work includes at least one of the following: a painting, a printed media, a 3D printed items, and a sculpted item.

19. The method of claim 1, wherein the original digital work comprises at least one of the following data modalities:

image data, video data, audio data, text data, 3D data, game data, movie data, sculpture data, vital sign data, health state data, a virtual reality rendering, software files, and financial data.

20. A system, comprising:
at least one processor; and
a non-transitory computer readable memory comprising instructions stored thereon that enable the at least one processor to:
store an original digital work associated with an original news story in a non-transitory computer readable memory;
generate a digital authentication token through execution of an implementation of at least one deterministic function on at least a portion of the original digital work and on digital identifying information associated with a publisher of the original news story and the original digital work;
publish the original digital work and the digital authentication token as a token/work pair, wherein the digital authentication token comprises an embedded link that points to the publisher of the original news story; and
enable validation processing that includes generating a validation score representing a validation of a suspect news story based on deterministic features derived from the authentication token and from at least a portion of the suspect news story, wherein the at least one deterministic function performs at least one of a pixel-to-pixel comparison, a descriptor comparison, and an optical character recognition comparison with the at least a portion of the original digital work, and wherein the deterministic features comprise a combination of outputs from at least two of the pixel-to-pixel comparison, the descriptor comparison, and the optical character recognition comparison.

21. A non-transitory computer readable memory comprising processor-executable instructions stored thereon, the instructions comprising at least the following instructions to:
store an original digital work associated with an original news story in a non-transitory computer readable memory;
generate a digital authentication token through execution of an implementation of at least one deterministic function on at least a portion of the original digital work and on digital identifying information associated with a publisher of the original news story and the original digital work;
publish the original digital work and the digital authentication token as a token/work pair, wherein the digital authentication token comprises an embedded link that points to the publisher of the original news story; and
enable validation processing that includes generating a validation score representing a validation of a suspect news story based on deterministic features derived from the authentication token and from at least a portion of the suspect news story, wherein the at least one deterministic function performs at least one of a pixel-to-pixel comparison, a descriptor comparison, and an optical character recognition comparison with the at least a portion of the original digital work, and wherein the deterministic features comprise a combination of outputs from at least two of the pixel-to-pixel comparison, the descriptor comparison, and the optical character recognition comparison.

* * * * *